(12) United States Patent
Moeller-Bertram et al.

(10) Patent No.: US 11,593,416 B2
(45) Date of Patent: *Feb. 28, 2023

(54) SYSTEM AND METHOD FOR AUTOMATED MULTI-DIMENSIONAL NETWORK MANAGEMENT

(71) Applicant: Mammoth Medical, LLC, Newport Beach, CA (US)

(72) Inventors: Tobias Moeller-Bertram, San Diego, CA (US); Christopher A. McDonald, Newport Beach, CA (US)

(73) Assignee: Mammoth Medical, LLC, Newport Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/138,072

(22) Filed: Dec. 30, 2020

(65) Prior Publication Data
US 2021/0191960 A1    Jun. 24, 2021

Related U.S. Application Data

(63) Continuation of application No. 16/505,514, filed on Jul. 8, 2019, now Pat. No. 10,885,083, which is a
(Continued)

(51) Int. Cl.
*G06F 16/335* (2019.01)
*G06N 5/022* (2023.01)
(Continued)

(52) U.S. Cl.
CPC .......... *G06F 16/337* (2019.01); *A61B 5/4848* (2013.01); *A61B 5/7264* (2013.01); *G06F 9/30036* (2013.01); *G06F 15/76* (2013.01); *G06K 9/623* (2013.01); *G06K 9/6232* (2013.01); *G06N 5/022* (2013.01); *G06N 20/00* (2019.01); *H04L 41/16* (2013.01);
(Continued)

(58) Field of Classification Search
None
See application file for complete search history.

(56) References Cited

U.S. PATENT DOCUMENTS 7,689,682 B1 *  3/2010  Eldering .............. H04L 67/104
                                                                 715/753
7,925,519 B2    4/2011  Greene
(Continued)

*Primary Examiner* — Lashonda Jacobs-Burton
(74) *Attorney, Agent, or Firm* — Mughal IP P.C.

(57) ABSTRACT

Systems, methods, and devices for automated provisioning are disclosed herein. The system can include a memory including a user profile database having n-dimension attributes of a user. The system can include a user device and a source device. The system can include a server that can: generate and store a user profile in the user profile database and generate and store a characterization vector from the user profile. The server can identify a service for provisioning, receive updates to at least some of the attributes of the first user, and trigger regeneration of the characterization vector from the received inputs. The server can: regenerate the characterization vector, determine an efficacy of the provisioned services, and automatically identify a second service for provisioning for a second user based on the efficacy of the provisioned services to the first user.

18 Claims, 15 Drawing Sheets

Related U.S. Application Data continuation of application No. 15/955,540, filed on Apr. 17, 2018, now Pat. No. 10,346,454.

(60) Provisional application No. 62/641,974, filed on Mar. 12, 2018, provisional application No. 62/486,358, filed on Apr. 17, 2017.

(51) Int. Cl.

| | |
|---|---|
| *G06N 20/00* | (2019.01) |
| *A61B 5/00* | (2006.01) |
| *G06F 15/76* | (2006.01) |
| *H04L 9/40* | (2022.01) |
| *G06F 9/30* | (2018.01) |
| *G06K 9/62* | (2022.01) |
| *H04L 41/16* | (2022.01) |
| *H04L 41/5054* | (2022.01) |
| *H04L 67/02* | (2022.01) |
| *H04L 67/52* | (2022.01) |
| *H04L 67/50* | (2022.01) |
| *A61B 5/022* | (2006.01) |
| *H04L 67/306* | (2022.01) |

(52) U.S. Cl.
CPC ...... *H04L 41/5054* (2013.01); *H04L 63/1433* (2013.01); *A61B 5/0022* (2013.01); *A61B 5/022* (2013.01); *H04L 67/02* (2013.01); *H04L 67/306* (2013.01); *H04L 67/52* (2022.05); *H04L 67/535* (2022.05)

(56) References Cited

U.S. PATENT DOCUMENTS

| | | | |
|---|---|---|---|
| 8,504,386 B2 | 8/2013 | Manning et al. | |
| 8,612,251 B2 | 12/2013 | Yourist et al. | |
| 8,781,859 B2 | 7/2014 | Manning et al. | |
| 8,799,023 B2 | 8/2014 | Chao | |
| 9,501,624 B2 | 11/2016 | Vishnubhatla et al. | |
| 9,800,506 B2 | 10/2017 | Vasseur | |
| 9,886,547 B2 | 2/2018 | Baniameri et al. | |
| 9,898,513 B2 * | 2/2018 | McGregor | G06F 16/2477 |
| 9,977,867 B2 | 5/2018 | Greene | |
| 10,353,937 B2 * | 7/2019 | Moeller-Bertram | G06N 20/00 |
| 10,614,111 B2 * | 4/2020 | Moeller-Bertram | G06N 5/022 |
| 2003/0174122 A1 * | 9/2003 | Dinges | G06F 3/0481 |
| | | | 345/156 |
| 2006/0154642 A1 * | 7/2006 | Scannell | G08B 7/066 |
| | | | 455/404.1 |
| 2007/0094188 A1 * | 4/2007 | Pandya | G16Z 99/00 |
| | | | 706/45 |
| 2007/0118399 A1 | 5/2007 | Avinash | |
| 2007/0203996 A1 | 8/2007 | Davitz | |
| 2010/0030418 A1 * | 2/2010 | Holland | G06F 11/008 |
| | | | 701/31.4 |
| 2012/0078062 A1 * | 3/2012 | Bagchi | A61B 5/00 |
| | | | 600/300 |
| 2013/0018954 A1 * | 1/2013 | Cheng | G06Q 30/02 |
| | | | 709/204 |
| 2014/0095201 A1 * | 4/2014 | Farooq | G16H 50/30 |
| | | | 705/3 |
| 2014/0164017 A1 | 6/2014 | Merkin | |
| 2015/0112710 A1 * | 4/2015 | Haber | G16H 50/50 |
| | | | 705/2 |
| 2015/0356250 A1 * | 12/2015 | Polimeni | G16H 10/60 |
| | | | 705/3 |
| 2016/0063212 A1 | 3/2016 | Monier | |
| 2016/0117484 A1 * | 4/2016 | Hanina | G16H 10/60 |
| | | | 705/3 |
| 2016/0350721 A1 | 12/2016 | Comerford | |
| 2017/0103181 A1 | 4/2017 | Czerska | |
| 2017/0132367 A1 * | 5/2017 | Cheng | G16H 50/80 |
| 2017/0169715 A1 * | 6/2017 | Alyuzcivitci | G06N 20/20 |
| 2017/0199189 A1 | 7/2017 | Wade | |
| 2017/0262445 A1 | 9/2017 | Jeon | |
| 2017/0030898 A1 | 10/2017 | Razavian | |
| 2017/0308981 A1 * | 10/2017 | Razavian | G16H 40/60 |
| 2017/0315825 A1 * | 11/2017 | Gordon | G06F 3/0482 |
| 2019/0005194 A1 * | 1/2019 | Eltoukhy | G16B 40/00 |
| 2021/0174800 A1 * | 6/2021 | Srinivasan | G16H 10/60 |

\* cited by examiner

SYSTEM AND METHOD FOR AUTOMATED MULTI-DIMENSIONAL NETWORK MANAGEMENT

CROSS-REFERENCES TO RELATED APPLICATIONS

This application is a continuation of U.S. patent application Ser. No. 16/505,514, filed on Jul. 8, 2019, and entitled "SYSTEM AND METHOD FOR AUTOMATED MULTI-DIMENSIONAL NETWORK MANAGEMENT," now U.S. Pat. No. 10,885,083, issued Jan. 5, 2021, which application is a continuation of U.S. patent application Ser. No. 15/955,540, filed on Apr. 17, 2018, and entitled "SYSTEM AND METHOD FOR AUTOMATED MULTI-DIMENSIONAL NETWORK MANAGEMENT," now U.S. Pat. No. 10,346,454, issued Jul. 9, 2019, which application claims the benefit of U.S. Provisional Application No. 62/641,974, filed on Mar. 12, 2018, and entitled "STATE-BASED CARE PROVISION LEARNING SYSTEM," and U.S. Provisional Application No. 62/486,358, filed on Apr. 17, 2017, and entitled, "STATE-BASED CARE PROVISION LEARNING SYSTEM," the entirety of each of which is hereby incorporated by reference herein.

BACKGROUND

A computer network, or data network, is a digital telecommunications network which allows nodes to share resources. In computer networks, computing devices exchange data with each other using connections between nodes (data links.) These data links are established over cable media such as wires or optic cables, or wireless media such as WiFi.

Network computer devices that originate, route and terminate the data are called network nodes. Nodes can include hosts such as personal computers, phones, servers as well as networking hardware. Two such devices can be said to be networked together when one device is able to exchange information with the other device, whether or not they have a direct connection to each other. In most cases, application-specific communications protocols are layered (i.e., carried as payload) over other more general communications protocols. This formidable collection of information technology requires skilled network management to keep it all running reliably.

Computer networks are increasingly used in diverse applications. However, many current networks do not adequately address issues arising in an increasingly digital world. Accordingly, new and improved systems, methods, and devices are desired.

BRIEF SUMMARY

One aspect of the present disclosure relates to an automated vector-characterization system. The system includes a memory including a user profile database containing n-dimension attributes of a user. The system includes a user device that can receive input from a first user and transmit the received input, and a source device that can receive source inputs and transmit the received source inputs. The system can include a server. The server can: receive the user input and the source inputs; generate and store a user profile in the user profile database, which user profile identifies n-dimension attributes of the first user; generate and store a characterization vector from the n-dimension attributes of the first user, which characterization vector can include four dimensions, each of which four dimensions can include a gradated classification indicator; identify a service for provisioning according to the characterization vector, the service including a digital component and a non-digital component; receive inputs indicating updates to at least some of the n-dimension attributes of the first user, which updates are received at least from the source device; trigger regeneration of the characterization vector from the received inputs; regenerate the characterization vector from the n-dimension attributes of the first user, which n-dimension attributes of the first user include the updates to at least some of the n-dimension attributes; generate a discrepancy vector characterizing a difference between the regenerated characterization vector and the characterization vector; determine an efficacy of the provisioned services based on the discrepancy vector; and automatically identify a second service for provisioning for a second user based on the efficacy of the provisioned services to the first user.

In some embodiments, the server can automatically deliver the digital component of the service for provisioning. In some embodiments, the digital component of the service for provisioning is automatically delivered subsequent to automated determination of fulfillment of at least one delivery criteria. In some embodiments, the determination of fulfillment of the at least one delivery criteria is made based on data contained in a data stream received from a messaging bus. In some embodiments, aspects of the characterization vector are linked to a plurality of services via a plurality of conditional probabilities. In some embodiments, the aspects of the characterization vector linked to the plurality of services via the plurality of conditional probabilities include at least some of the n-dimension attributes of the first user.

In some embodiments, the service for provisioning is identified according to an Artificial Intelligence ("AI") machine-learning model. In some embodiments, the AI machine-learning model is trained to output a service for provisioning based on the characterization vector. In some embodiments, the server can ingest at least a portion of the characterization vector into the AI machine-learning model. In some embodiments, the AI machine-learning model is trained to output a service intensity based on the characterization vector. In some embodiments, the four dimensions include: a physical dimension; an emotional dimension; an interaction dimension; and a vulnerability dimension.

One aspect of the present disclosure relates to a method for automated characterization-vector based prediction. The method includes: receiving a user input from a user device and a source input from a source device; generating and storing a user profile in a user profile database, which user profile identifies n-dimension attributes of a first user; generating and storing a characterization vector from the n-dimension attributes of the first user, which characterization vector can have four dimensions, each of which four dimensions can include a gradated classification indicator; identifying a service for provisioning to the first user according to the characterization vector, the service including a digital component and a non-digital component; receiving inputs indicating updates to at least some of the n-dimension attributes of the first user, which updates are received at least from the source device; triggering regeneration of the characterization vector from the received inputs; regenerating the characterization vector from the n-dimension attributes of the first user, which n-dimension attributes of the first user include the updates to at least some of the n-dimension attributes; generating a discrepancy vector characterizing a difference between the regenerated characterization vector and the characterization vector; determining an efficacy of the provisioned services based on the discrepancy vector; and automatically identifying a second service for provisioning for a second user based on the efficacy of the provisioned services to the first user.

In some embodiments, the method includes automatically delivering the digital component of the service for provisioning. In some embodiments, the digital component of the service for provisioning is automatically delivered subsequent to automated determination of fulfillment of at least one delivery criteria. In some embodiments, the determination of fulfillment of the at least one delivery criteria is made based on data contained in a data stream received from a messaging bus. In some embodiments, aspects of the characterization vector are linked to a plurality of services via a plurality of conditional probabilities. In some embodiments, the aspects of the characterization vector linked to the plurality of services via the plurality of conditional probabilities include at least some of the n-dimension attributes of the first user.

In some embodiments, the service for provisioning is identified according to an AI machine-learning model. In some embodiments, the AI machine-learning model is trained to output a service for provisioning based on the characterization vector. In some embodiments, the method includes ingesting at least a portion of the characterization vector into the AI machine-learning model. In some embodiments, the AI machine-learning model is trained to output a service intensity based on the characterization vector. In some embodiments, the four dimensions include: a physical dimension; an emotional dimension; an interaction dimension; and a vulnerability dimension.

One aspect of the present disclosure relates to an automated multi-dimensional network management system. The system includes: a memory including: a user profile database having n-dimension attributes of a user; and a multi-dimensional network having a plurality of nodes linked by a plurality of edges. The system can include a user device that can receive input from a first user and transmit the received input, and a source device that can receive source inputs and transmit the received source inputs. The system can include a server. The server can: receive the user input and the source inputs; generate and store a user profile in the user profile database, which user profile identifies n-dimension attributes of the first user; determine a current state of the first user based on the user profile; generate a risk profile according to the current state of the first user, which risk profile identifies a likelihood of an adverse outcome within a time frame; identify a remediation via an AI machine-learning model to mitigate the likelihood of the adverse outcome, which remediation is identified based on the user profile and the current state of the first user; identify a data insufficiency, which data insufficiency prevents at least one of: complete determination of the current state of the first user; complete generation of the risk profile; or complete identification of the remediation; identify a service for provisioning to the first user, which service is identified to remedy the data insufficiency, the service including a digital component and a non-digital component; provisioning the identified service and resolving the data insufficiency; automatically determining resolution of the data insufficiency; upon determining resolution of the data insufficiency, completing the at least one of: determination of the current state of the first user; generation of the risk profile; or identification of the remediation; and provide a remediation to the first user.

In some embodiments, the server can automatically deliver the digital component of the service for provisioning. In some embodiments, the digital component of the service for provisioning is automatically delivered subsequent to automated determination of fulfillment of at least one delivery criteria. In some embodiments, the server can automatically schedule provisioning of the service. In some embodiments, scheduling the provisioning of the service includes: retrieving user location information from the user device; determining a classification of the service for provisioning; identifying potential service locations based on a combination of location of the potential service locations, user location information, and service location attributes.

In some embodiments, the user location information retrieved from the user device can include current location information and location history information. In some embodiments, the location history information identifies historic trends in user location. In some embodiments, the service location attributes identify service types provided at the service location. In some embodiments, the server can: receive inputs indicating updates to at least some of the n-dimension attributes of the first user, which updates are received at least from the source device; trigger updating of the user profile based on the received inputs; and automatically identify a second service for provisioning to the first user. In some embodiments, the second service is identified based on the updated user profile. In some embodiments, the second service can include a plurality of timed and automatically triggered reminders directing the first user to complete an action.

One aspect of the present disclosure relates to a method of multi-dimensional network management. The method includes: receiving a user input from a first user device and source inputs from at least one source device; generating and storing a user profile in the user profile database, which user profile identifies n-dimension attributes of the first user; determining a current state of the first user based on the user profile; generating a risk profile according to the current state of the first user, which risk profile identifies a likelihood of an adverse outcome within a time frame; identifying a remediation via an AI machine-learning model to mitigate the likelihood of the adverse outcome, which remediation is identified based on the user profile and the current state of the first user; identifying a data insufficiency, which data insufficiency prevents at least one of: complete determination of the current state of the first user; complete generation of the risk profile; or complete identification of the remediation; identifying a service for provisioning to the first user, which service is identified to remedy the data insufficiency, the service including a digital component and a non-digital component; provisioning the identified service and resolving the data insufficiency; automatically determining resolution of the data insufficiency; upon determining resolution of the data insufficiency, completing the at least one of: determination of the current state of the first user; generation of the risk profile; or identification of the remediation; and providing a remediation to the first user via the first user device.

In some embodiments, the method includes automatically delivering the digital component of the service for provisioning. In some embodiments, the digital component of the service for provisioning is automatically delivered subsequent to automated determination of fulfillment of at least one delivery criteria. In some embodiments, the method includes automatically scheduling providing of the service. In some embodiments, scheduling the provisioning of the service includes: retrieving user location information from the user device; determining a classification of the service for provisioning; identifying potential service locations based on a combination of location of the potential service locations, user location information, and service location attributes.

In some embodiments, the user location information retrieved from the user device includes current location information and location history information. In some embodiments, the location history information identifies historic trends in user location. In some embodiments, the service location attributes identify service types provided at the service location.

In some embodiments, the method includes: receiving inputs indicating updates to at least some of the n-dimension attributes of the first user, which updates are received at least from the source device; triggering updating of the user profile based on the received inputs; and automatically identifying a second service for provisioning to the first user, which second service is identified based on the updated user profile. In some embodiments, the second service includes a plurality of timed and automatically triggered reminders directing the first user to complete an action.

One aspect of the present disclosure relates to an automated multi-dimensional network management system. The system includes a memory including: a user profile database identifying attributes of a plurality of users, and a model database including a plurality of machine-learning models trained to generate text in response to received inputs characterizing attributes of a subject-user and at least one recipient-user. In some embodiments, the plurality of users include a plurality of classes of users. In some embodiments, the plurality of classes of users includes at least one class of subject-users and at least two classes of recipient-users. The system can include a source device that can receive source inputs and transmit the received source inputs, which source inputs relate to an attribute of the subject-user. The system can include a recipient device that can receive recipient inputs and transmit the received recipient inputs, which recipient inputs identify an attribute of the recipient-user. The system can include a server. The server can: receive a plurality of inputs identifying attributes of the subject-user; receive at least one input identifying an attribute of the recipient-user; select a machine-learning model based on the at least one attribute of the recipient-user; ingest received inputs into the machine-learning model; receive text output from the machine-learning model, which text output is customized to the recipient-user; and automatically generate and deliver a message to the recipient-user device comprising at least portions of the text output.

In some embodiments, the server can to receive a report request for the recipient-user device. In some embodiments, the report request includes data identifying the attribute of the recipient-user. In some embodiments, at least some of the plurality of inputs identifying attributes of the subject-user are received from the source device. In some embodiments, the system includes an electrical analysis machine. In some embodiments, the electrical analysis automatically generates data indicative of an attribute of the subject-user from an interaction with the subject-user. In some embodiments, the electrical analysis machine automatically provides the data indicative of the attribute of the subject-user to the server.

In some embodiments, the server can receive feedback data indicative of a responsiveness of the delivered message to the report request. In some embodiments, the server can receive a second report request from a second recipient-user. In some embodiments, the second report request includes at least one input identifying an attribute of the second recipient-user. In some embodiments, the attribute of the second recipient-user is different than the attribute of the recipient-user. In some embodiments, the server can: select a second machine-learning model based on the attribute of the second recipient-user; and automatically generate and deliver a second message to the second recipient-user including an output of the second machine-learning model. In some embodiments, the server can: ingest the plurality of inputs identifying attributes of the subject-user into the second machine-learning model; and receive text output from the second machine-learning model, wherein the text output is customized to the second recipient-user.

One aspect of the present disclosure relates to a method of machine-learning input-based data autogeneration. The method includes: receiving at a server a plurality of inputs from a source device identifying attributes of a subject-user; receiving at the server at least one input from a recipient-user device identifying at least one attribute of a recipient-user; selecting a machine-learning model from a model database based on the at least one attribute of the recipient-user, the model database including a plurality of machine-learning models trained to generate text in response to received inputs characterizing attributes of a subject-user and at least one recipient-user; ingesting received inputs into the machine-learning model; receiving text output from the machine-learning model, which text output is customized to the recipient-user; and automatically generating and delivering a message to the recipient-user device comprising at least portions of the text output.

In some embodiments, the method includes receiving a report request for the recipient-user device, which report request includes data identifying the attribute of the recipient-user. In some embodiments, at least some of the plurality of inputs identifying attributes of the subject-user are received from the source device. In some embodiments, the method includes receiving data identifying of an attribute of the subject-user at the server from an electrical analysis machine. In some embodiments, the electrical analysis machine automatically generates data from an interaction with the subject-user. In some embodiments, the electrical analysis machine automatically provides the data identifying the attribute of the subject-user to the server.

In some embodiments, the method includes receiving feedback data indicative of a responsiveness of the delivered message to the report request. In some embodiments, the method includes receiving a second report request from a second recipient-user. In some embodiments, the second report request includes at least one input identifying an attribute of the second recipient-user. In some embodiments, the attribute of the second recipient-user is different than the attribute of the recipient-user.

In some embodiments, the method includes: selecting a second machine-learning model based on the attribute of the second recipient-user; and automatically generating and delivering a second message to the second recipient-user including an output of the second machine-learning model. In some embodiments, the method includes: ingesting the plurality of inputs identifying attributes of the subject-user into the second machine-learning model; and receiving text output from the second machine-learning model. In some embodiments, the text output is customized to the second recipient-user.

Further areas of applicability of the present disclosure will become apparent from the detailed description provided hereinafter. It should be understood that the detailed description and specific examples, while indicating various embodi-

Figure 1:
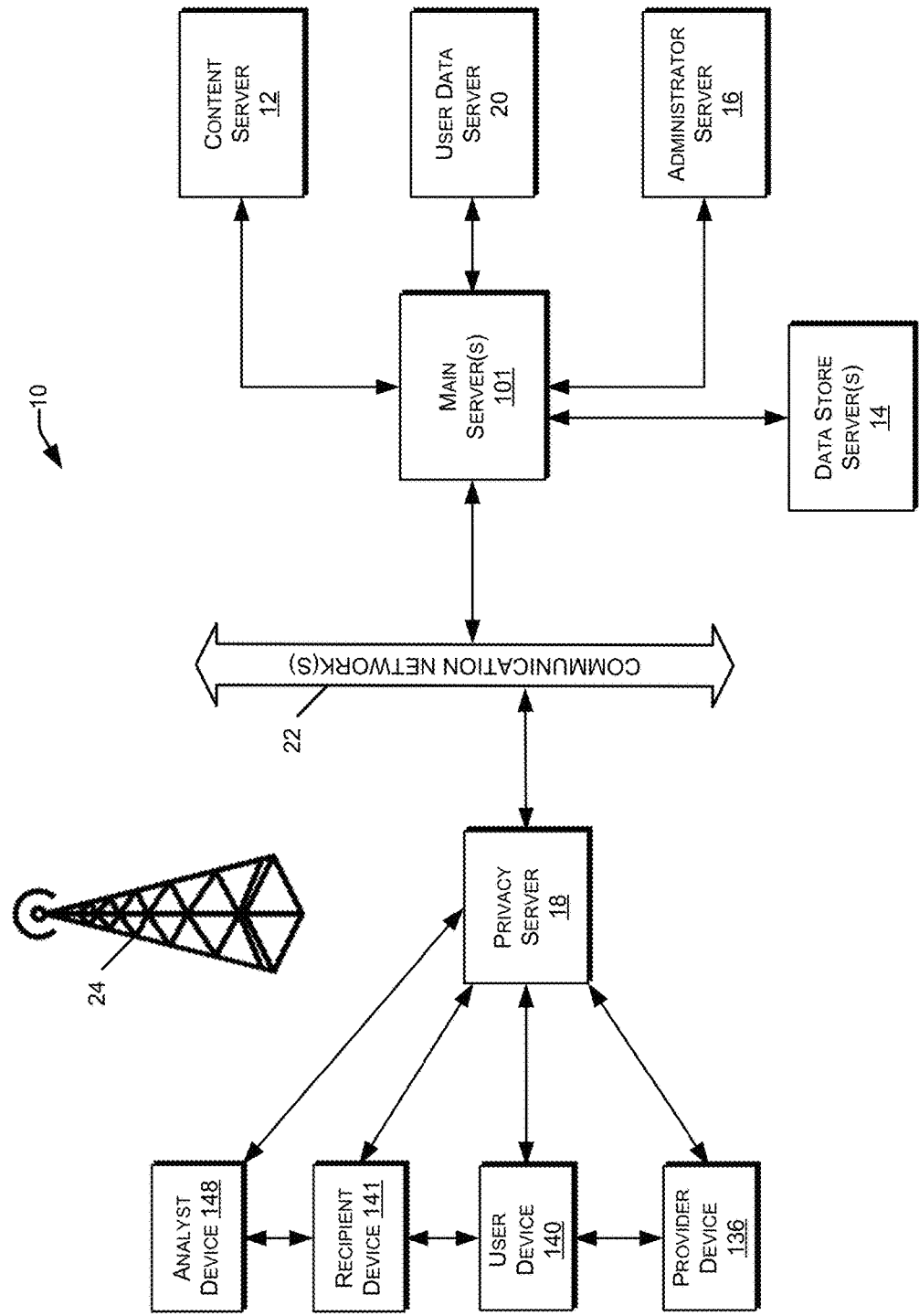
FIG. 1 is a block diagram illustrating various components of an automated provisioning network.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

Some aspects of the present disclosure relate to new methods, systems, and/or devices for gathering information from multiple sources relating to a single user. This information identifies attributes of the users, each of which corresponds to a dimension in an n-dimensional space. Some or all of these dimensions can be orthogonal. These dimensions can relate to, for example, one or several physical attributes of the user, one or several mental attributes of the user, one or several social attributes of the user, one or several spiritual attributes of the user, one or several socio-economic attributes of the user, or the like. These attributes can be aggregated and conformed to a desired and/or common format. These attributes can then be used to form a vector that overall characterizes the user. This vector can comprise a magnitude and a direction. In some embodiments, one or both of the magnitude and the direction of the vector can be associated with an overall evaluation of the user, and changes to the magnitude and/or direction of the vector can correspond to a change in the overall evaluation of the user. In some embodiments, the magnitude and/or direction of the vector can be used to identify one or several interventions for the user, a risk level for the user, or the like.

In some embodiments, the attributes of the user can be tracked over time, and the vector associated with the user can be tracked over time. Changes to the attributes and/or to the vector can be indicative of a change to the status of the user such as, for example, a change to the health and/or well-being of the user.

In some aspects, the present disclosure relates to a networked database comprising a hybrid network formed of a plurality of n-number of networks, each of which networks comprising a plurality of nodes. In some embodiments, this can include a first network comprising nodes that each correspond one or several user states, a second network comprising nodes that each correspond to one or several user characteristics, a third network comprising nodes that each correspond to one or several remedial actions, a fourth network comprising nodes that each correspond to one or several outcomes. In some embodiments, nodes from the plurality of networks can be interlinked via a plurality of edges, wherein each edge connects a pair of nodes. Each of these edges can be associated with a conditional probability that can characterize the probability of the truth of one of the nodes in the pair of nodes linked by the edge based on the status of the other of the nodes in the pair of nodes linked by the edge.

In some aspects, these networks can be customizable based on one or several attributes of the user that can be stored in a user profile. These attributes of the user can be the same attributes as those used to form the vector, can be different attributes than those used to form the vector, or can be partially the same attributes as those used to form the vector. In some embodiments, conditional probabilities associated with edges connecting nodes can vary based on these attributes. For example, an attribute may indicate a strong user preference for or against a type of action. This attribute may thus impact conditional probabilities associated with edges linking nodes related to that action.

The hybrid network can be used to customize interventions provided to the user. This can include customization according to efficacy, according to a cost function, according to user preference, or the like. In some embodiments, this customization can be made based on the expected outcome for a user having the attributes of the current user, similarly, in some embodiments this cost function can be a customized cost function tailored to a user having the attributes of the user.

Some aspects of the present disclosure relate to the autogeneration of data, text, and/or messages based on a plurality of inputs. These inputs can include one or several inputs provided by the apparent author of the text and one or several inputs provided by the recipient of the data, text, and/or messages. Thus, the autogeneration of the data, text, and/or messages can be dependent on inputs by both the apparent creator of the text as well as by the recipient of the data, text, and/or messages. In some embodiments, based on a single set of inputs by the apparent author of the data, text, and/or messages, a plurality of data, text, and/or messages can be outputted, each corresponding to one or several inputs received from one or several recipients.

With reference now to FIG. 1, a block diagram is shown illustrating various components of an automated provisioning network 10 which implements and supports certain embodiments and features described herein. In some embodiments, the automated provisioning network 10 can comprise one or several physical components and/or one or several virtual components such as, for example, one or several cloud computing components. In some embodiments, the automated provisioning network 10 can comprise a mixture of physical and cloud computing components.

Automated provisioning network 10 may include one or more main servers 101. As discussed below in more detail, main servers 101 may be any desired type of server including, for example, a rack server, a tower server, a miniature server, a blade server, a mini rack server, a mobile server, an ultra-dense server, a super server, or the like, and may include various hardware components, for example, a motherboard, a processing unit, memory systems, hard drives, network interfaces, power supplies, etc. Main server 101 may include one or more server farms, clusters, or any other appropriate arrangement and/or combination or computer servers. Main server 101 may act according to stored instructions located in a memory subsystem of the server 101, and may run an operating system, including any commercially available server operating system and/or any other operating systems discussed herein.

The automated provisioning network 10 may include one or more data store servers 14, such as database servers and file-based storage systems. The database servers 14 can access data that can be stored on a variety of hardware components. These hardware components can include, for example, components forming tier 0 storage, components forming tier 1 storage, components forming tier 2 storage, and/or any other tier of storage. In some embodiments, tier 0 storage refers to storage that is the fastest tier of storage in the database server 14, and particularly, the tier 0 storage is the fastest storage that is not RAM or cache memory. In some embodiments, the tier 0 memory can be embodied in solid state memory such as, for example, a solid-state drive (SSD) and/or flash memory.

In some embodiments, the tier 1 storage refers to storage that is one or several higher performing systems in the memory management system, and that is relatively slower than tier 0 memory, and relatively faster than other tiers of memory. The tier 1 memory can be one or several hard disks that can be, for example, high-performance hard disks. These hard disks can be one or both of physically or communicatively connected such as, for example, by one or several fiber channels. In some embodiments, the one or several disks can be arranged into a disk storage system, and specifically can be arranged into an enterprise class disk storage system. The disk storage system can include any desired level of redundancy to protect data stored therein, and in one embodiment, the disk storage system can be made with grid architecture that creates parallelism for uniform allocation of system resources and balanced data distribution.

In some embodiments, the tier 2 storage refers to storage that includes one or several relatively lower performing systems in the memory management system, as compared to the tier 1 and tier 2 storages. Thus, tier 2 memory is relatively slower than tier 1 and tier 0 memories. Tier 2 memory can include one or several SATA-drives (e.g., Serial AT Attachment drives) or one or several NL-SATA drives.

In some embodiments, the one or several hardware and/or software components of the database server 14 can be arranged into one or several storage area networks (SAN), which one or several storage area networks can be one or several dedicated networks that provide access to data storage, and particularly that provides access to consolidated, block level data storage. A SAN typically has its own network of storage devices that are generally not accessible through the local area network (LAN) by other devices. The SAN allows access to these devices in a manner such that these devices appear to be locally attached to the user device.

Data stores 14 may comprise stored data relevant to the functions of the automated provisioning network 10. Illustrative examples of data stores 14 that may be maintained in certain embodiments of the automated provisioning network 10 are described throughout the application. In some embodiments, multiple data stores may reside on a single server 14, either using the same storage components of server 14 or using different physical storage components to assure data security and integrity between data stores. In other embodiments, each data store may have a separate dedicated data store server 14.

Automated provisioning network 10 also may include one or more provider devices 136, also referred to herein as source devices 136, user devices 140, recipient devices 141, and/or analyst devices 148. Source devices 136, user devices 140, recipient devices 141, and analyst devices 148 may display content received via the automated provisioning network 10, and may support various types of user interactions with the content. Source devices 136, user devices 140, recipient devices 141, and analyst devices 148 may include mobile devices such as smartphones, tablet computers, personal digital assistants, and wearable computing devices. Such mobile devices may run a variety of mobile operating systems and may be enabled for Internet, e-mail, short message service (SMS), Bluetooth®, mobile radio-frequency identification (M-RFID), and/or other communication protocols. Other source devices 136, user devices 140, recipient devices 141, and analyst devices 148 may be general purpose personal computers or special-purpose computing devices including, by way of example, personal computers, laptop computers, workstation computers, projection devices, and interactive room display systems. Additionally, source devices 136, user devices 140, recipient devices 141, and analyst devices 148 may be any other electronic devices, such as a thin-client computers, an Internet-enabled gaming systems, business or home appliances, and/or a personal messaging devices, capable of communicating over network(s) 22.

In different contexts of automated provisioning networks 10, source devices 136, user devices 140, recipient devices 141, and analyst devices 148 may correspond to different types of specialized devices, for example, clinician devices, patient devices and analyst devices in an care provisioning network and/or care management network, employee devices and presentation devices in a company network, different gaming devices in a gaming network, etc. In some embodiments, source devices 136, user devices 140, recipient devices 141, and analyst devices 148 may operate in the same physical location, such as in a clinic, exam room, surgical room, etc. In such cases, the devices may contain components that support direct communications with other nearby devices, such as wireless transceivers and wireless communications interfaces, Ethernet sockets or other Local Area Network (LAN) interfaces, etc. In other implementations, the source devices 136, user devices 140, recipient devices 141, and analyst devices 148 need not be used at the same location, but may be used in remote geographic locations in which each source device 136, user device 140, recipient devices 141, and analyst device 148 may use security features and/or specialized hardware (e.g., hardware-accelerated SSL and HTTPS, WS-Security, firewalls, etc.) to communicate with the main server 101 and/or other remotely located devices 136, 140, 141, 148. Additionally, different source devices 136, user devices 140, recipient devices 141, and analyst devices 148 may be assigned different designated roles, such as presenter devices, user devices, source devices, analyst devices, or the like, and in such cases the different devices may be provided with additional hardware and/or software components to provide content and support user capabilities not available to the other devices.

The automated provisioning network 10 also may include a privacy server 18 that maintains private user information at the privacy server 18 while using applications or services hosted on other servers. For example, the privacy server 18 may be used to maintain private data of a user within one jurisdiction even though the user is accessing an application hosted on a server (e.g., the main server 101) located outside the jurisdiction. In such cases, the privacy server 18 may intercept communications between a source device 136, a user device 140, and/or analyst device 148 and other devices that include private user information. The privacy server 18 may create a token or identifier that does not disclose the private information and may use the token or identifier when communicating with the other servers and systems, instead of using the user's private information.

As illustrated in FIG. 1, the main server 101 may be in communication with one or more additional servers, such as a content server 12, a user data server 20, and/or an administrator server 16. Each of these servers may include some or all of the same physical and logical components as the main server(s) 101, and in some cases, the hardware and software components of these servers 12, 16, 20 may be incorporated into the main server(s) 101, rather than being implemented as separate computer servers.

Content server 12 may include hardware and software components to generate, store, and maintain the content resources for distribution to user devices 140 and other devices in the network 10. For example, in automated provisioning networks 10 used for professional training and educational purposes, content server 12 may include data stores of training materials, presentations, plans, syllabi, reviews, evaluations, interactive programs and simulations, course models, course outlines, and various training interfaces that correspond to different materials and/or different types of user devices 140. In automated provisioning networks 10 used for media distribution, interactive gaming, and the like, a content server 12 may include media content files such as music, movies, television programming, games, and advertisements.

User data server 20 may include hardware and software components that store and process data for multiple users relating to each user's activities and usage of the automated provisioning network 10. For example, the main server 101 may record and track each user's system usage, including their source device 136, user device 140, and/or analyst device 148, content resources accessed, and interactions with other source devices 136, user devices 140, and/or analyst devices 148. This data may be stored and processed by the user data server 20, to support user tracking and analysis features. For instance, in the professional training and educational contexts, the user data server 20 may store and analyze each user's training materials viewed, presentations attended, courses completed, interactions, evaluation results, and the like. The user data server 20 may also include a repository for user-generated material, such as evaluations and tests completed by users, and documents and assignments prepared by users. In some embodiments, the user data server 20 can further store information relating to a user's certificates, certifications, qualifications, completed trainings, licensing, licensed jurisdictions, or the like. In some embodiments, the user data server 20 can further store information relating to the status of the user's certificates, certifications, qualifications, completed trainings, and/or licensing. This can include whether and/or when the user's certificates, certifications, qualifications, completed trainings, and/or licensings expire and/or lapse. In the context of media distribution and interactive gaming, the user data server 20 may store and process resource access data for multiple users (e.g., content titles accessed, access times, data usage amounts, gaming histories, user devices and device types, etc.).

Administrator server 16 may include hardware and software components to initiate various administrative functions at the main server 101 and other components within the automated provisioning network 10. For example, the administrator server 16 may monitor device status and performance for the various servers, data stores, and/or user devices 136, 140, 141, 148 in the automated provisioning network 10. When necessary, the administrator server 16 may add or remove devices from the network 10, and perform device maintenance such as providing software updates to the devices in the network 10. Various administrative tools on the administrator server 16 may allow authorized users to set user access permissions to various content resources, monitor resource usage by users and devices 136, 140, 141, 148, and perform analyses and generate reports on specific network users and/or devices (e.g., resource usage tracking reports, training evaluations, etc.).

The automated provisioning network 10 may include one or more communication networks 22. Although only a single network 22 is identified in FIG. 1, the automated provisioning network 10 may include any number of different communication networks between any of the computer servers and devices shown in FIG. 1 and/or other devices described herein. Communication networks 22 may enable communication between the various computing devices, servers, and other components of the automated provisioning network 10. As discussed below, various implementations of automated provisioning networks 10 may employ different types of networks 22, for example, computer networks, telecommunications networks, wireless networks, and/or any combination of these and/or other networks.

The automated provisioning network 10 may include one or several navigation systems or features including, for example, the Global Positioning System ("GPS"), GALILEO (e.g., Europe's global positioning system), or the like, or location systems or features including, for example, one or several transceivers that can determine location of the one or several components of the automated provisioning network 10 via, for example, triangulation. All of these are depicted as navigation system 24.

In some embodiments, navigation system 24 can include or several features that can communicate with one or several components of the automated provisioning network 10 including, for example, with one or several of the source devices 136, with one or several of the user devices 140, and/or with one or several of the analyst devices 148. In some embodiments, this communication can include the transmission of a signal from the navigation system 24 which signal is received by one or several components of the automated provisioning network 10 and can be used to determine the location of the one or several components of the automated provisioning network 10.

Figure 2:
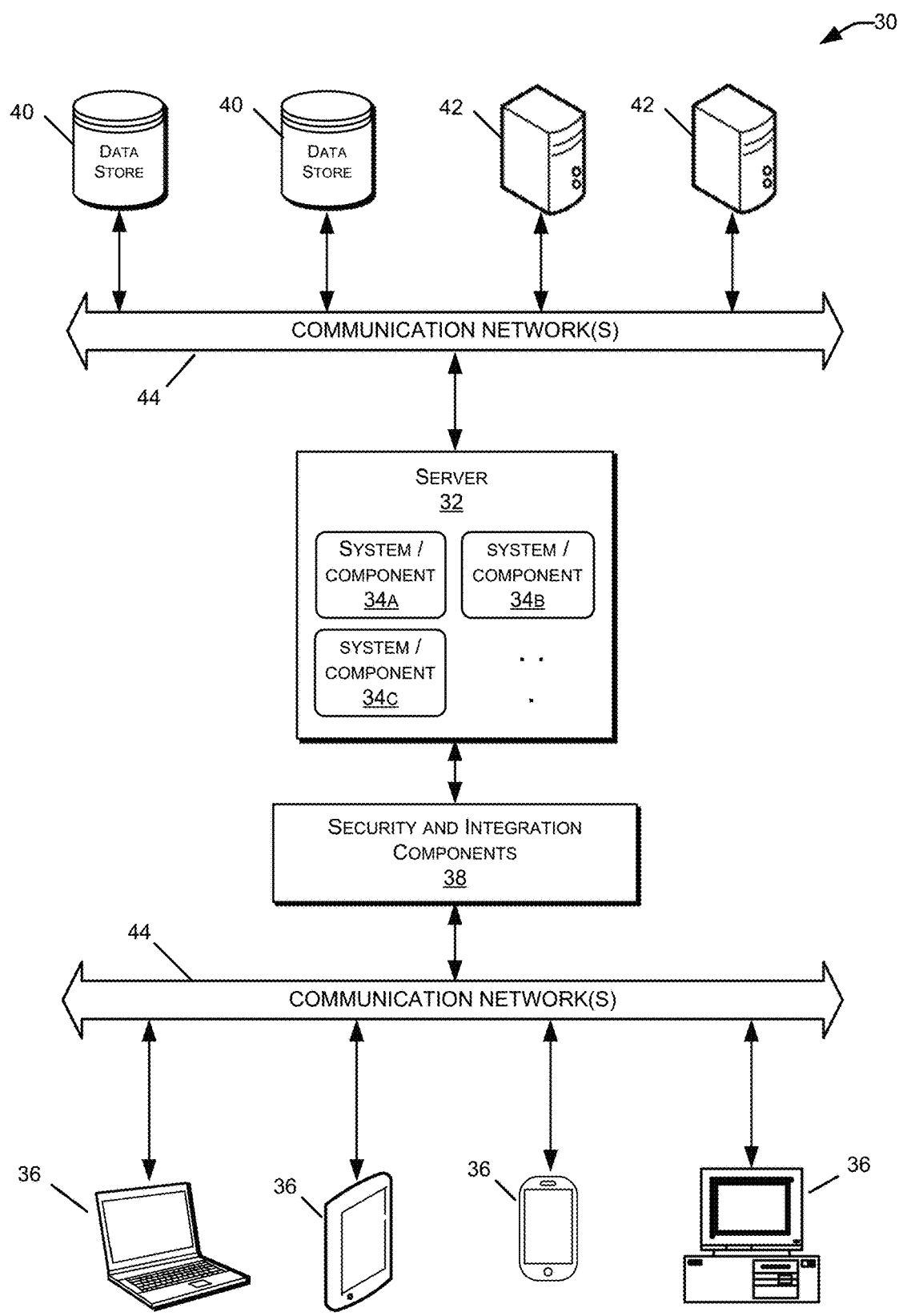
FIG. 2 is a schematic illustration of one embodiment of a distributed computing environment.

With reference to FIG. 2, an illustrative distributed computing environment 30 is shown including a computer server 32, four client computing devices 36, and other components that may implement certain embodiments and features described herein. In some embodiments, the server 32 may correspond to the main server 101 discussed above in FIG. 1, and the client computing devices 36 may correspond to one or more of the source devices 136, the user devices 140, recipient devices 141, and/or the analyst devices 148. However, the computing environment 30 illustrated in FIG. 2 may correspond to any other combination of devices and servers configured to implement a client-server model or other distributed computing architecture.

Client devices 36 may be configured to receive and execute client applications over one or more networks 44. Such client applications may be web browser based applications and/or standalone software applications, such as mobile device applications. Server 32 may be communicatively coupled with the client devices 36 via one or more communication networks 44. Client devices 36 may receive client applications from server 32 or from other application providers (e.g., public or private application stores). Server 32 may be configured to run one or more server software applications or services, for example, web-based or cloud-based services, to support content distribution and interaction with client devices 36. Users operating client devices 36 may in turn utilize one or more client applications (e.g., virtual client applications) to interact with server 32 to utilize the services provided by these components.

Various different subsystems and/or components 34 may be implemented on server 32. Users operating the client devices 36 may initiate one or more client applications to use services provided by these subsystems and components. The subsystems and components within the server 32 and client devices 36 may be implemented in hardware, firmware, software, or combinations thereof. Various different system configurations are possible in different distributed computing systems 30 and automated provisioning networks 10. The embodiment shown in FIG. 2 is thus one example of a distributed computing system and is not intended to be limiting.

Although exemplary computing environment 30 is shown with four client computing devices 36, any number of client computing devices may be supported. Other devices, such as specialized sensor devices, etc., may interact with client devices 36 and/or server 32.

As shown in FIG. 2, various security and integration components 38 may be used to send and manage communications between the server 32 and user devices 36 over one or more communication networks 44. The security and integration components 38 may include separate servers, such as web servers and/or authentication servers, and/or specialized networking components, such as firewalls, routers, gateways, load balancers, and the like. In some cases, the security and integration components 38 may correspond to a set of dedicated hardware and/or software operating at the same physical location and under the control of the same entities as server 32. For example, components 38 may include one or more dedicated web servers and network hardware in a datacenter or a cloud infrastructure. In other examples, the security and integration components 38 may correspond to separate hardware and software components which may be operated at a separate physical location and/or by a separate entity.

Security and integration components 38 may implement various security features for data transmission and storage, such as authenticating users and restricting access to unknown or unauthorized users. In various implementations, security and integration components 38 may provide, for example, a file-based integration scheme or a service-based integration scheme for transmitting data between the various devices in the automated provisioning network 10. Security and integration components 38 also may use secure data transmission protocols and/or encryption for data transfers, for example, File Transfer Protocol (FTP), Secure File Transfer Protocol (SFTP), and/or Pretty Good Privacy (PGP) encryption.

In some embodiments, one or more web services may be implemented within the security and integration components 38 and/or elsewhere within the automated provisioning network 10. Such web services, including cross-domain and/or cross-platform web services, may be developed for enterprise use in accordance with various web service standards, such as RESTful web services (i.e., services based on the Representation State Transfer (REST) architectural style and constraints), and/or web services designed in accordance with the Web Service Interoperability (WS-I) guidelines. Some web services may use the Secure Sockets Layer (SSL) or Transport Layer Security (TLS) protocol to provide secure connections between the server 32 and user devices 36. SSL or TLS may use HTTP or HTTPS to provide authentication and confidentiality. In other examples, web services may be implemented using REST over HTTPS with the OAuth open standard for authentication, or using the WS-Security standard which provides for secure SOAP (e.g., Simple Object Access Protocol) messages using Extensible Markup Language (XML) encryption. In other examples, the security and integration components 38 may include specialized hardware for providing secure web services. For example, security and integration components 38 may include secure network appliances having built-in features such as hardware-accelerated SSL and HTTPS, WS-Security, and firewalls. Such specialized hardware may be installed and configured in front of any web servers, so that any external devices may communicate directly with the specialized hardware.

Communication network(s) 44 may be any type of network familiar to those skilled in the art that can support data communications using any of a variety of commercially-available protocols, including without limitation, TCP/IP (transmission control protocol/Internet protocol), SNA (systems network architecture), IPX (Internet packet exchange), Secure Sockets Layer (SSL) or Transport Layer Security (TLS) protocols, Hyper Text Transfer Protocol (HTTP) and Secure Hyper Text Transfer Protocol (HTTPS), Bluetooth®, Near Field Communication (NFC), and the like. Merely by way of example, network(s) 44 may be local area networks (LAN), such as one based on Ethernet, Token-Ring, and/or the like. Network(s) 44 also may be wide-area networks, such as the Internet. Networks 44 may include telecommunication networks such as a public switched telephone networks (PSTNs), or virtual networks such as an intranet or an extranet. Infrared and wireless networks (e.g., using the Institute of Electrical and Electronics (IEEE) 802.11 protocol suite or other wireless protocols) also may be included in networks 44.

Computing environment 30 also may include one or more data stores 40 and/or back-end servers 42. In certain examples, the data stores 40 may correspond to data store server(s) 14 discussed above in FIG. 1, and back-end servers 42 may correspond to the various back-end servers 12, 14, 16, 20. Data stores 40 and servers 42 may reside in the same datacenter or may operate at a remote location from server 32. In some cases, one or more data stores 40 may reside on a non-transitory storage medium within the server 32. Other data stores 40 and back-end servers 42 may be remote from server 32 and configured to communicate with server 32 via one or more networks 44. In certain embodiments, data stores 40 and back-end servers 42 may reside in a storage-area network (SAN), or may use storage-as-a-service (STaaS) architectural model.

Figure 3:
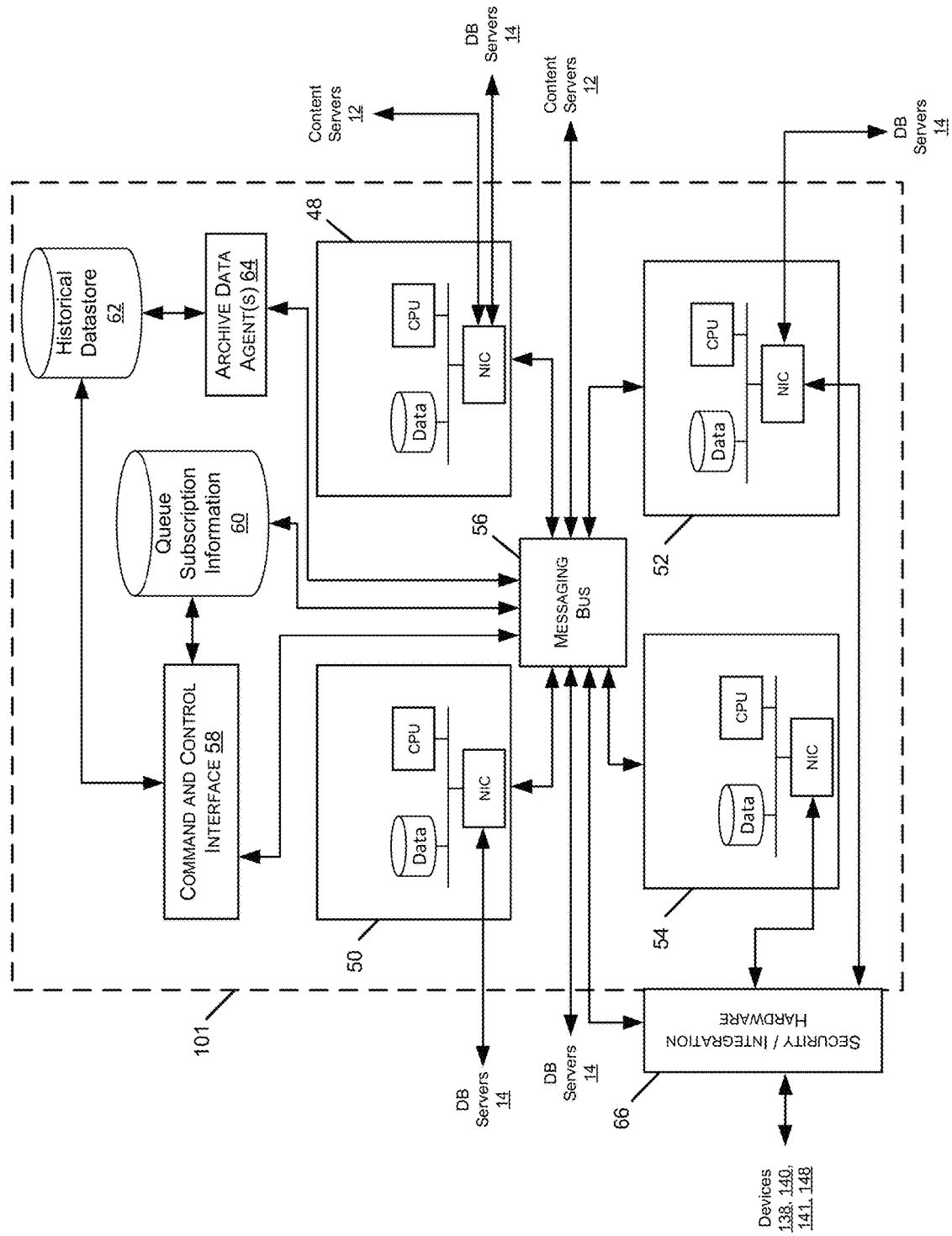
FIG. 3 is a schematic illustration of one embodiment of a server of the automated provisioning network.

With reference now to FIG. 3, a block diagram is shown illustrating an embodiment of one or more main servers 101 within an automated provisioning network 10. In such an embodiment, main server 101 performs internal data gathering and processing of streamed content along with external data gathering and processing. Other embodiments could have either all external or all internal data gathering. This embodiment allows reporting timely information that might be of interest to the reporting party or other parties. In this embodiment, the main server 101 can monitor gathered information from several sources to allow it to make timely business and/or processing decisions based upon that information. For example, reports of user actions and/or responses, as well as the status and/or results of one or several processing tasks could be gathered and reported to the main server 101 from a number of sources.

Internally, the main server 101 gathers information from one or more internal components 48-54. The internal components 48-54 gather and/or process information relating to such things as: services provided to patient-users, also referred to herein as subject-users; data gathered from patient-users; inputs from provider-users; inputs provided by recipient-users, patient-user state; patient-user characteristics; patient-user progress; etc. The internal components 48-54 can report the gathered and/or generated information in real-time, near real-time or along another time line. To account for any delay in reporting information, a time stamp or staleness indicator can inform others of how timely the information was sampled. The main server 101 can opt to allow third parties to use internally or externally gathered information that is aggregated within the server 101 by subscription to the automated provisioning network 10.

A command and control (CC) interface 58 configures the gathered input information to an output of data streams, also referred to herein as content streams. APIs for accepting gathered information and providing data streams are provided to third parties external to the server 101 who want to subscribe to data streams. The server 101 or a third party can design as yet undefined APIs using the CC interface 58. The server 101 can also define authorization and authentication parameters using the CC interface 58 such as authentication, authorization, login, and/or data encryption. CC information is passed to the internal components 48-54 and/or other components of the automated provisioning network 10 through a channel separate from the gathered information or data stream in this embodiment, but other embodiments could embed CC information in these communication channels. The CC information allows throttling information reporting frequency, specifying formats for information and data streams, deactivation of one or several internal components 48-54 and/or other components of the automated provisioning network 10, updating authentication and authorization, etc.

The various data streams that are available can be researched and explored through the CC interface 58. Those data stream selections for a particular subscriber, which can be one or several of the internal components 48-54 and/or other components of the automated provisioning network 10, are stored in the queue subscription information database 60. The server 101 and/or the CC interface 58 then routes selected data streams to processing subscribers that have selected delivery of a given data stream. Additionally, the server 101 also supports historical queries of the various data streams that are stored in a historical data store 62 as gathered by an archive data agent 64. Through the CC interface 58 various data streams can be selected for archiving into the historical data store 62.

Components of the automated provisioning network 10 outside of the server 101 can also gather information that is reported to the server 101 in real-time, near real-time, or along another time line. There is a defined API between those components and the server 101. Each type of information or variable collected by server 101 falls within a defined API or multiple APIs. In some cases, the CC interface 58 is used to define additional variables to modify an API that might be of use to processing subscribers. The additional variables can be passed to all processing subscribers or just a subset of the processing subscribers. For example, a component of the automated provisioning network 10 outside of the server 101 may report a user response, but define an identifier of that user as a private variable that would not be passed to processing subscribers lacking access to that user and/or authorization to receive that user data. Processing subscribers having access to that user and/or authorization to receive that user data would receive the subscriber identifier along with the response reported to that component. Encryption and/or unique addressing of data streams or sub-streams can be used to hide the private variables within the messaging queues.

The source devices 136, user devices 140, and/or analyst devices 148 communicate with the server 101 through security and/or integration hardware 66. The communication with security and/or integration hardware 66 can be encrypted or not. For example, a socket using a TCP connection could be used. In addition to TCP, other transport layer protocols like Control Transmission Protocol (SCTP) and User Datagram Protocol (UDP) could be used in some embodiments to intake the gathered information. A protocol such as SSL could be used to protect the information over the TCP connection. Authentication and authorization can be performed to any user devices 140 and/or supervisor device interfacing to the server 101. The security and/or integration hardware 66 receives the information from one or several of the user devices 140 and/or the analyst devices 148 by providing the API and any encryption, authorization, and/or authentication. In some cases, the security and/or integration hardware 66 reformats or rearranges this received information The messaging bus 56, also referred to herein as a messaging queue or a messaging channel, can receive information from the internal components of the server 101 and/or components of the automated provisioning network 10 outside of the server 101 and distribute the gathered information as a data stream to any processing subscribers that have requested the data stream from the messaging queue 56. As indicated in FIG. 3, processing subscribers are indicated by a connector to the messaging bus 56, the connector having an arrow head pointing away from the messaging bus 56. In some examples, only data streams within the messaging queue 56 that a particular processing subscriber has subscribed to may be read by that processing subscriber if received at all. Gathered information sent to the messaging queue 56 is processed and returned in a data stream in a fraction of a second by the messaging queue 56. Various multicasting and routing techniques can be used to distribute a data stream from the messaging queue 56 that a number of processing subscribers have requested. Protocols such as Multicast or multiple Unicast could be used to distributed streams within the messaging queue 56. Additionally, transport layer protocols like TCP, SCTP and UDP could be used in various embodiments.

Through the CC interface 58, an external or internal processing subscriber can be assigned one or more data streams within the messaging queue 56. A data stream is a particular type of messages in a particular category. For example, a data stream can comprise all of the data reported to the messaging bus 56 by a designated set of components. One or more processing subscribers could subscribe and receive the data stream to process the information and make a decision and/or feed the output from the processing as gathered information fed back into the messaging queue 56. Through the CC interface 58 a developer can search the available data streams or specify a new data stream and its API. The new data stream might be determined by processing a number of existing data streams with a processing subscriber.

The automated provisioning network 10 has internal processing subscribers 48-54 that process assigned data streams to perform functions within the server 101. Internal processing subscribers 48-54 could perform functions such as: identifying and/or tracking services provided to patient-users; gathering data from patient-users; gathering data from provider-users; identifying and/or tracking patient-user state; identifying and/or tracking one or several patient-user characteristics; identifying and/or tracking patient-user progress; recommending services and/or user actions; or the like. The internal processing subscribers 48-54 can decide filtering and weighting of records from the data stream. To the extent that decisions are made based upon analysis of the data stream, each data record is time stamped to reflect when the information was gathered such that additional credibility could be given to more recent results, for example. Other embodiments may filter out records in the data stream that are from an unreliable source or stale. For example, a particular contributor of information may prove to have less than optimal gathered information and that could be weighted very low or removed altogether.

Internal processing subscribers 48-54 may additionally process one or more data streams to provide different information to feed back into the messaging queue 56 to be part of a different data stream. For example, hundreds of user devices 140 could provide responses that are put into a data stream on the messaging queue 56. An internal processing subscriber 48-54 could receive the data stream and process it to determine the difficulty of one or several data packets provided to one or several users and supply this information back onto the messaging queue 56 for possible use by other internal and external processing subscribers.

As mentioned above, the CC interface 58 allows the automated provisioning network 10 to query historical messaging queue 56 information. An archive data agent 64 listens to the messaging queue 56 to store data streams in a historical database 62. The historical database 62 may store data streams for varying amounts of time and may not store all data streams. Different data streams may be stored for different amounts of time.

With regard to the components 48-54, the main server(s) 101 may include various server hardware and software components that manage the content resources within the automated provisioning network 10 and provide interactive and adaptive content to users on various user devices 140. For example, main server(s) 101 may provide instructions to and receive information from the other devices within the automated provisioning network 10, in order to manage and transmit content resources, user data, and server or client applications executing within the network 10.

Figure 4:
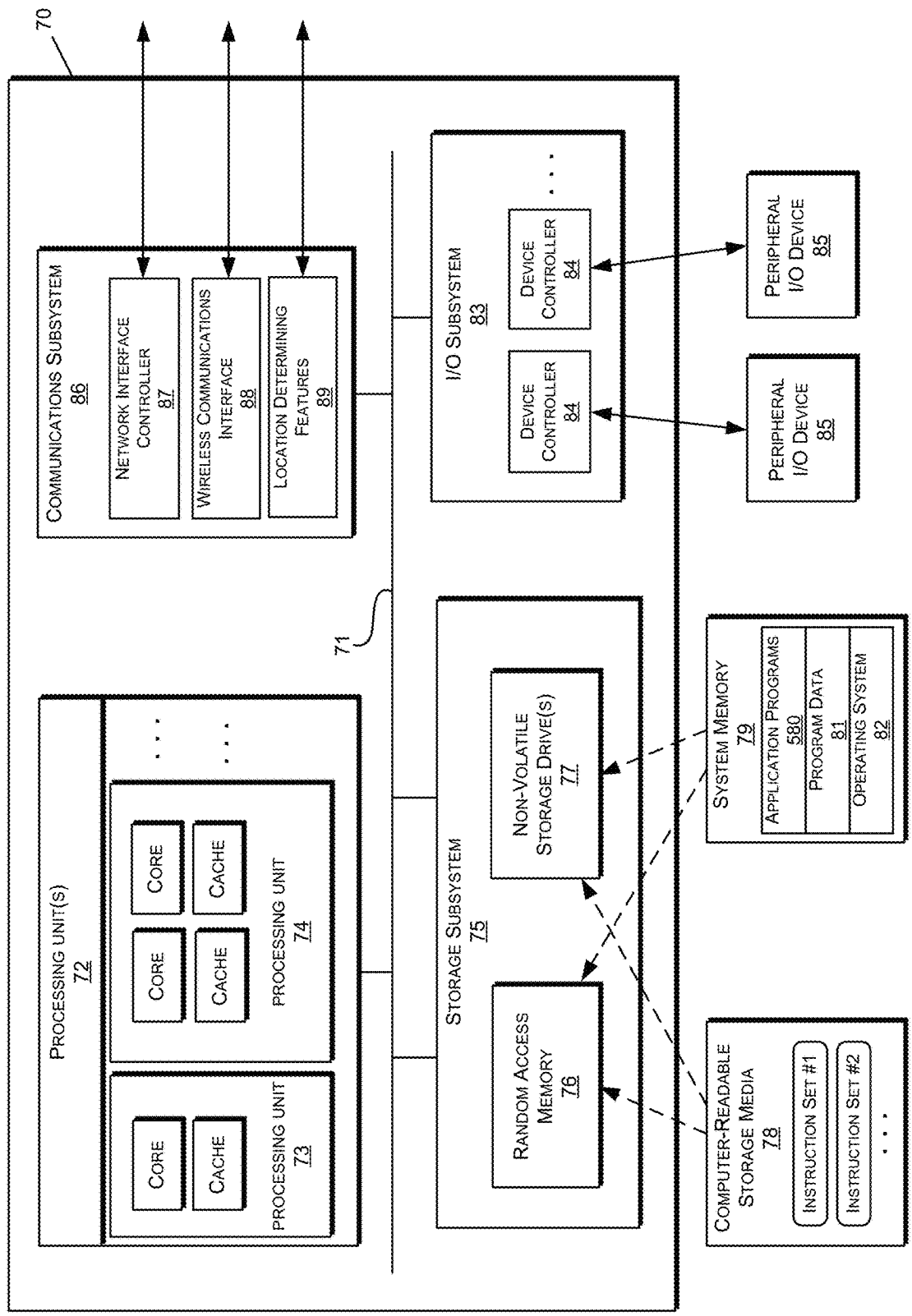
FIG. 4 is a schematic illustration of one embodiment of a computer system.

With reference now to FIG. 4, a block diagram of an illustrative computer system is shown. The system 70 may correspond to any of the computing devices or servers of the automated provisioning network 10 described above, or any other computing devices described herein, and specifically can include, for example, one or several of the source devices 136, one or several of the user devices 140, and/or one or several of the analyst device 148, and/or any of the servers 101, 12, 14, 16, 18, 20. In this example, computer system 70 includes processing units 72 that communicate with a number of peripheral subsystems via a bus subsystem 71. These peripheral subsystems include, for example, a storage subsystem 75, an I/O subsystem 83, and a communications subsystem 86.

Bus subsystem 71 provides a mechanism for letting the various components and subsystems of computer system 70 communicate with each other as intended. Although bus subsystem 71 is shown schematically as a single bus, alternative embodiments of the bus subsystem may utilize multiple buses. Bus subsystem 71 may be any of several types of bus structures including a memory bus or memory controller, a peripheral bus, and a local bus using any of a variety of bus architectures. Such architectures may include, for example, an Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, which can be implemented as a Mezzanine bus manufactured to the IEEE P1386.1 standard.

Processing unit 72, which may be implemented as one or more integrated circuits (e.g., a conventional microprocessor or microcontroller), controls the operation of computer system 70. One or more processors, including single core and/or multicore processors, may be included in processing unit 72. As shown in the figure, processing unit 72 may be implemented as one or more independent processing units 73 and/or 74 with single or multicore processors and processor caches included in each processing unit. In other embodiments, processing unit 72 may also be implemented as a quad-core processing unit or larger multicore designs (e.g., hexa-core processors, octo-core processors, ten-core processors, or greater.

Processing unit 72 may execute a variety of software processes embodied in program code, and may maintain multiple concurrently executing programs or processes. At any given time, some or all of the program code to be executed can be resident in processor(s) 72 and/or in storage subsystem 75. In some embodiments, computer system 70 may include one or more specialized processors, such as digital signal processors (DSPs), outboard processors, graphics processors, application-specific processors, and/or the like.

I/O subsystem 83 may include device controllers 84 for one or more user interface input devices and/or user interface output devices 85. User interface input and output devices 85 may be integral with the computer system 70 (e.g., integrated audio/video systems, and/or touchscreen displays), or may be separate peripheral devices which are attachable/detachable from the computer system 70. The I/O subsystem 83 may provide one or several outputs to a user by converting one or several electrical signals to user perceptible and/or interpretable form, and may receive one or several inputs from the user by generating one or several electrical signals based on one or several user-caused interactions with the I/O subsystem such as the depressing of a key or button, the moving of a mouse, the interaction with a touchscreen or trackpad, the interaction of a sound wave with a microphone, or the like.

Input devices 85 may include a keyboard, pointing devices such as a mouse or trackball, a touchpad or touch screen incorporated into a display, a scroll wheel, a click wheel, a dial, a button, a switch, a keypad, audio input devices with voice command recognition systems, microphones, and other types of input devices. Input devices 85 may also include three dimensional (3D) mice, joysticks or pointing sticks, gamepads and graphic tablets, and audio/visual devices such as speakers, digital cameras, digital camcorders, portable media players, webcams, image scanners, fingerprint scanners, barcode reader 3D scanners, 3D printers, laser rangefinders, and eye gaze tracking devices. Additional input devices 85 may include, for example, motion sensing and/or gesture recognition devices that enable users to control and interact with an input device through a natural user interface using gestures and spoken commands, eye gesture recognition devices that detect eye activity from users and transform the eye gestures as input into an input device, voice recognition sensing devices that enable users to interact with voice recognition systems through voice commands, medical imaging input devices, MIDI keyboards, digital musical instruments, and the like.

Output devices 85 may include one or more display subsystems, indicator lights, or non-visual displays such as audio output devices, etc. Display subsystems may include, for example, cathode ray tube (CRT) displays, flat-panel devices, such as those using a liquid crystal display (LCD) or plasma display, light-emitting diode (LED) displays, projection devices, touch screens, and the like. In general, use of the term "output device" is intended to include all possible types of devices and mechanisms for outputting information from computer system 70 to a user or other computer. For example, output devices 85 may include, without limitation, a variety of display devices that visually convey text, graphics, and audio/video information such as monitors, printers, speakers, headphones, automotive navigation systems, plotters, voice output devices, and modems.

Computer system 70 may comprise one or more storage subsystems 75, comprising hardware and software components used for storing data and program instructions, such as system memory 79 and computer-readable storage media 78. The system memory 79 and/or computer-readable storage media 78 may store program instructions that are loadable and executable on processing units 72, as well as data generated during the execution of these programs.

Depending on the configuration and type of computer system 70, system memory 79 may be stored in volatile memory (such as random access memory (RAM) 76) and/or in non-volatile storage drives 77 (such as read-only memory (ROM), flash memory, etc.). The RAM 76 may contain data and/or program modules that are immediately accessible to and/or presently being operated and executed by processing units 72. In some implementations, system memory 79 may include multiple different types of memory, such as static random access memory (SRAM) or dynamic random access memory (DRAM). In some implementations, a basic input/output system (BIOS), containing the basic routines that help to transfer information between elements within computer system 70, such as during start-up, may typically be stored in the non-volatile storage drives 77. By way of example, and not limitation, system memory 79 may include application programs 80, such as client applications, Web browsers, mid-tier applications, server applications, etc., program data 81, and an operating system 82.

Storage subsystem 75 also may provide one or more tangible computer-readable storage media 78 for storing the basic programming and data constructs that provide the functionality of some embodiments. Software (programs, code modules, instructions) that when executed by a processor provide the functionality described herein may be stored in storage subsystem 75. These software modules or instructions may be executed by processing units 72. Storage subsystem 75 may also provide a repository for storing data used in accordance with the present invention.

Storage subsystem 75 may also include a computer-readable storage media reader that can further be connected to computer-readable storage media 78. Together and, optionally, in combination with system memory 79, computer-readable storage media 78 may comprehensively represent remote, local, fixed, and/or removable storage devices plus storage media for temporarily and/or more permanently containing, storing, transmitting, and retrieving computer-readable information.

Computer-readable storage media 78 containing program code, or portions of program code, may include any appropriate media known or used in the art, including storage media and communication media, such as, but not limited to, volatile and non-volatile, removable and non-removable media implemented in any method or technology for storage and/or transmission of information. This can include tangible computer-readable storage media such as RAM, ROM, electronically erasable programmable ROM (EEPROM), flash memory or other memory technology, CD-ROM, digital versatile disk (DVD), or other optical storage, magnetic cassettes, magnetic tape, magnetic disk storage or other magnetic storage devices, or other tangible computer readable media. This can also include nontangible computer-readable media, such as data signals, data transmissions, or any other medium which can be used to transmit the desired information and which can be accessed by computer system 70.

By way of example, computer-readable storage media 78 may include a hard disk drive that reads from or writes to non-removable, nonvolatile magnetic media, a magnetic disk drive that reads from or writes to a removable, nonvolatile magnetic disk, and an optical disk drive that reads from or writes to a removable, nonvolatile optical disk such as a CD ROM, DVD, and Blu-Ray® disk, or other optical media. Computer-readable storage media 78 may include, but is not limited to, Zip® drives, flash memory cards, universal serial bus (USB) flash drives, secure digital (SD) cards, DVD disks, digital video tape, and the like. Computer-readable storage media 78 may also include, solid-state drives (SSD) based on non-volatile memory such as flash-memory based SSDs, enterprise flash drives, solid state ROM, and the like, SSDs based on volatile memory such as solid state RAM, dynamic RAM, static RAM, DRAM-based SSDs, magnetoresistive RAM (MRAM) SSDs, and hybrid SSDs that use a combination of DRAM and flash memory based SSDs. The disk drives and their associated computer-readable media may provide non-volatile storage of computer-readable instructions, data structures, program modules, and other data for computer system 70.

Communications subsystem 86 may provide a communication interface from computer system 70 and external computing devices via one or more communication networks, including local area networks (LANs), wide area networks (WANs) (e.g., the Internet), and various wireless telecommunications networks. As illustrated in FIG. 4, the communications subsystem 86 may include, for example, one or more network interface controllers (NICs) 87, such as Ethernet cards, Asynchronous Transfer Mode NICs, Token Ring NICs, and the like, as well as one or more wireless communications interfaces 88, such as wireless network interface controllers (WNICs), wireless network adapters, and the like. As illustrated in FIG. 4, the communications subsystem 86 may include, for example, one or more location determining features 89 such as one or several navigation system features and/or receivers, and the like. Additionally and/or alternatively, the communications subsystem 86 may include one or more modems (telephone, satellite, cable, ISDN), synchronous or asynchronous digital subscriber line (DSL) units, FireWire® interfaces, USB® interfaces, and the like. Communications subsystem 88 also may include radio frequency (RF) transceiver components for accessing wireless voice and/or data networks (e.g., using cellular telephone technology, advanced data network technology, such as 3G, 4G or EDGE (enhanced data rates for global evolution), WiFi (IEEE 802.11 family standards, or other mobile communication technologies, or any combination thereof), global positioning system (GPS) receiver components, and/or other components.

The various physical components of the communications subsystem 86 may be detachable components coupled to the computer system 70 via a computer network, a FireWire® bus, or the like, and/or may be physically integrated onto a motherboard of the computer system 70. Communications subsystem 86 also may be implemented in whole or in part by software.

In some embodiments, communications subsystem 86 may also receive input communication in the form of structured and/or unstructured data feeds, event streams, event updates, and the like, on behalf of one or more users who may use or access computer system 70. For example, communications subsystem 86 may be configured to receive data feeds in real-time from users of social networks and/or other communication services, web feeds such as Rich Site Summary (RSS) feeds, and/or real-time updates from one or more third party information sources (e.g., external data source 313). Additionally, communications subsystem 86 may be configured to receive data in the form of continuous data streams, which may include event streams of real-time events and/or event updates (e.g., sensor data applications, financial tickers, network performance measuring tools, clickstream analysis tools, automobile traffic monitoring, etc.). Communications subsystem 86 may output such structured and/or unstructured data feeds, event streams, event updates, and the like to one or more data stores 14 that may be in communication with one or more streaming data source computers coupled to computer system 70.

Due to the ever-changing nature of computers and networks, the description of computer system 70 depicted in the figure is intended only as a specific example. Many other configurations having more or fewer components than the system depicted in the figure are possible. For example, customized hardware might also be used and/or particular elements might be implemented in hardware, firmware, software, or a combination. Further, connection to other computing devices, such as network input/output devices, may be employed. Based on the disclosure and teachings provided herein, a person of ordinary skill in the art will appreciate other ways and/or methods to implement the various embodiments.

Figure 5:
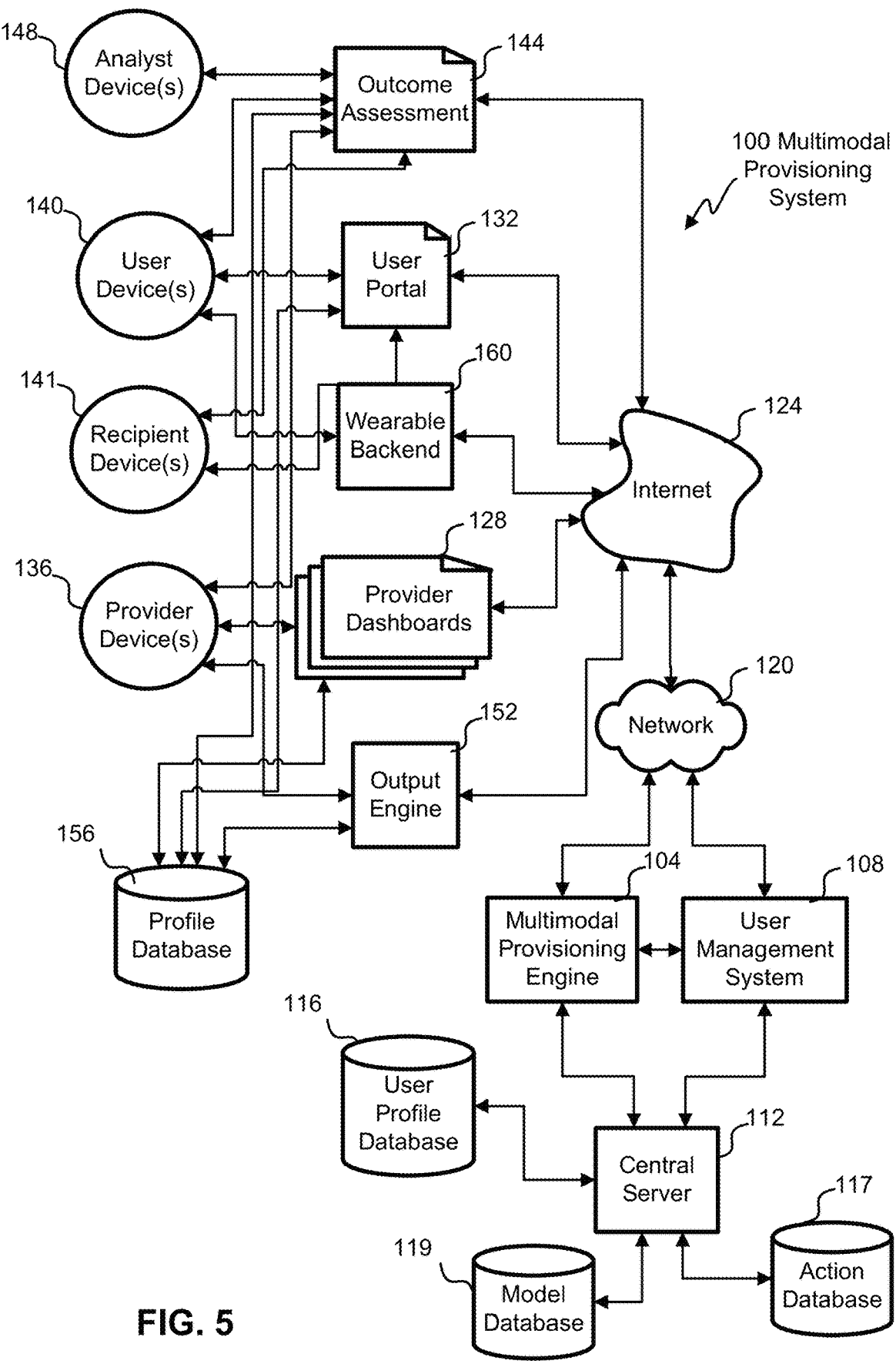
FIG. 5 is an illustration of one embodiment of a multi-modal provisioning system.

Referring initially to FIG. 5, an embodiment of a multimodal provisioning system 100 is shown that systemically manages user care, also referred to herein as user service provisioning. The multimodal provisioning system 100 can be embodied in all or portions of the automated provisioning network 10. In some embodiments, three different groups of users interact with the multimodal provisioning system 100, specifically, users, which can be, for example, users under care, also referred to herein as user service recipients or patient-users, providers, also referred to as provider-users, providing the service provisioning, and outcome analysts who gauge recovery and/or the effectiveness of the provided services in changing the patient-user's condition or state. Each group of users have their respective source devices 136, user devices 140, and/or analyst devices 148, to interface with the multimodal provisioning system 100 that include smartphone apps, web portals, application software.

The source devices 136 interact with several interfaces, specifically, an output engine 152, provider dashboards 128 and an outcome assessment interface 144. The provider dashboards 128 display customized screens that may be designed by the provider differently for different users, service provisioning lines, groups of users, service provisioning modules, etc., which are stored as profiles in an interface profile database 156 The progression of user progress, which progress can include recovery, can be graphed by user or any group of users, for example showing the global health composite score, also referred to herein as a user composite characterization. In some embodiments, this composite characterization can be a tensor or vector, and is referred to herein as a summary vector, a user vector and/or a characterization-vector. In some embodiments, the characterization-vector can be created from all or portions of the user composite characterization and the characterization-vector can map one or several scored criteria to an n-dimensional space. In some embodiments, all or portions of the n-dimensional space can correspond to high risk users and/or users requiring complex care. In some embodiments, different locations within the n-dimensional space can correspond to different levels of care.

The output engine 152 allows the provider, also referred to herein as the source, to review content such as, for example, charts in a bespoke and/or summary manner. Different service provisioning modules, user groups, and users can trigger different profiles that can be stored in the interface profile database 156 for the output engine 152. These different profiles can cause an interface provided by the output engine 152 to morph into different interfaces, formats, data display and query forms according to the context. For example, when a source is interacting with a particular user, that user's data can be displayed with personal information relevant for the workflow of service provisioning along with forms for any missing information or information requiring verification. The output engine 152 can read back notes associated with the user with a spoken avatar voice that allows natural language input queries with the note. Each audio note can also be customized such that the narrative is context aware according to the relevant profile 156.

Users have computers, tablets, smart phones, and wearables as user devices 140 that can interact with the multimodal provisioning system 100. Wearables can be proprietary to the multimodal provisioning system 100 or accessed with an API to a third-party system (not shown). In this embodiment, the wearable user devices 140 interface with the wearable backend 160 such that activity and vitals can be fed into the multimodal provisioning system 100 to confirm performance of steps in a service provisioning workflow and vitals during service provisioning. The user devices 140 can also connect to the outcome assessment interface 144 so that the user can see their progression and evaluations of their current state and/or condition.

The user portal 132 is the primary resource for the users while interacting with the multimodal provisioning system 100. Prior to any interaction or service provisioning, any desired information can be gathered from the user via the user portal 132. This gathered information can be stored for use in connection with a future interaction with the user and/or between a source and the user. In some embodiments, electronic forms can accumulate the questions that may originate from a number of service provisioning modules. Some or all of these accumulated questions can be presented cohesively without requiring redundant information. Certain questions are aimed to assess emotional and physical well-being as service provisioning improves a user's current state and/or condition. The user portal 132 allows checking-in for a service event such as an appointment and/or printing or generating a badge or barcode for use at the office reception. Scanning of a printed or screen-displayed barcode allows avoiding the conventional form completion processes for a service provisioning appointment. The calendar function on the user device 140 is accessible to cross-reference availability for scheduling service provisioning. Intelligence on commute times is used to avoid meetings scheduled to close together to allow for travel given typical traffic patterns at the scheduled time for a proposed appointment. The user portal can further facilitate gathering information such as attributes of one or several users, and specifically of one or several recipient-users. In some embodiments, these recipient-users can access the multimodal provisioning system 100 via one or several recipient devices 141. These recipient-users can, for example, be intended recipient of data outputs of the multimodal provisioning system 100, such as, for example, outputs characterizing one or several attributes of a subject-user, outputs characterizing one or several attributes or results of services provided to the subject-user, or the like. In some embodiments, the recipient-user can be the subject-user, can be the provider-user, can be an obligated-user such as, for example, a representative of an insurance company, or the like.

Outcome analysts gather information to assess progression through the service provisioning process. In some embodiment, progression through the service provisioning process and/or compliance with the regimen is automatically determined and/or associated data is automatically gathered. Some clinical test results, also referred to herein as assessment results are automatically gathered along with information from other testing equipment, which testing equipment can include medical testing equipment. In some embodiments, some or all of the gathered information is available to the analyst devices 148 using the outcome assessment interface 144. The outcome analyst will often use the analyst device 148 to manually gather additional information, administer testing and choreograph other information gathering using the outcome assessment interface.

The outcome assessment interface 144, user portal 132, wearable backend 160, provider dashboards 128, and output engine 152 are shown being hosted in the cloud, but some or all could also be behind-the-firewall and hosted on the other side of the network 120 or a combination of both hosted and cloud footprints in various embodiments. The internet 124 is connected to the network 120 across a firewall (not shown).

A multimodal care engine 104, also referred to herein as a multimodal provisioning engine 104, and user management system 108 interact with a central server 112 that is coupled to a user profile database 116. In some embodiments, the user profile database can comprise one or several user profiles, which can each comprise n-dimension attributes of one or several users. In some embodiments, each user can have a unique user profile that can include, n-dimension attributes of that user. These attributes can be gathered by the multimodal provisioning system 100 and specifically can be gathered from, for example, the user device 140, the source device 136, or any other device, or equipment connected to the multimodal provisioning system 100. The central server 112 can receive inputs from other components of the multimodal provisioning system 100 including, for example, the source device 136, the user device 140, and/or any other device, or equipment connected to the multimodal provisioning system 100. The central server 112 could be a third party product from any number of different vendors. The functionality of the multimodal provisioning system 100 is agnostic to the different underlying central servers 112 that might be used. Information on the user, service provisioning performed, scheduling, regimens assigned, etc. are stored in the user profile database 116 to the extent that the central server 112 supports those data fields. Where the additional data is not supported by a particular third-party central server 112, it would be stored in elsewhere in the multimodal provisioning engine 104 and/or the user management system 108.

The multimodal provisioning system 100 can include an action database 117. The action database can comprise data relating to one or several services for provisioning to the subject-user and/or actions for taking by the subject-user. In some embodiments, the action database 117 can comprise a multi-dimensional network comprising a plurality of nodes that can be linked by a plurality of edges. In some embodiments, this multi-dimensional network can include a first network comprising nodes that each correspond one or several user states, a second network comprising nodes that each correspond to one or several user characteristics, a third network comprising nodes that each correspond to one or several remedial actions, a fourth network comprising nodes that each correspond to one or several outcomes. In some embodiments, nodes from the plurality of networks can be interlinked via a plurality of edges, wherein each edge connects a pair of nodes. Each of these edges can be associated with a conditional probability that can characterize the probability of the truth of one of the nodes in the pair of nodes linked by the edge based on the status of the other of the nodes in the pair of nodes linked by the edge.

In some aspects, this multi-dimensional network can be customizable based on one or several attributes of the user that can be stored in a user profile. These attributes of the user can be the same attributes as those used to for the vector, can be different attributes than those used to form the vector, or can be partially the same attributes as those used to form the vector. In some embodiments, conditional probabilities associated with edges connecting nodes can vary based on these attributes. For example, an attribute may indicate a strong user preference for or against a type of action. This attribute may thus impact conditional probabilities associated with edges linking nodes related to that action.

Figure 6:
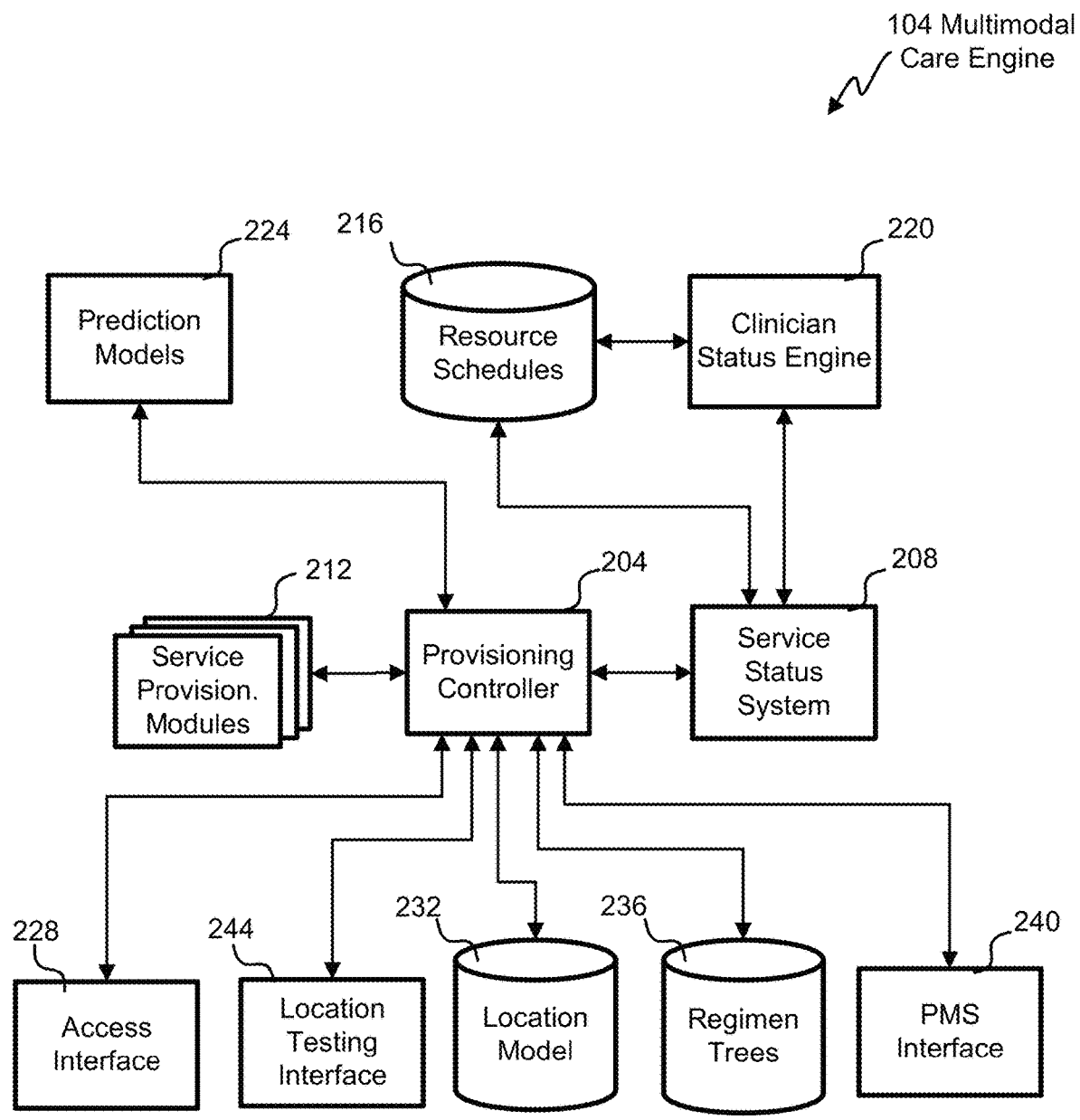
FIG. 6 is an illustration of an embodiment of a multimodal provisioning engine of the multimodal provisioning system.

Referring next to FIG. 6, an embodiment of a multimodal provisioning engine 104 is shown in detail. In some embodiments, the multimodal provisioning engine 104 can comprise one of the internal components 48-54 of the server 101, and in some embodiments, the components of the multimodal provisioning engine 104 can comprise the internal components 48-54 of the server 101. In such an embodiment, the component of the multimodal provisioning engine 104 may be linked by the messaging bus 56 and may coordinate actions and/or act based on the data stream received from the messaging bus 56 according to an event-based design.

A provisioning controller 204 choreographs the operation of the multimodal provisioning engine 104. For each service provisioning line state model, there is a service provisioning module 212 that has all the interface elements, testing questions, data fields, workflow the service provisioning line, etc. necessary to control, interact and manage the service provisioning line. For example, one service provisioning line could be opioid addiction counseling and the service provisioning module would have screens for the source to gather information on current opioid use, screens to gather survey information from the user directly or with an outcome analyst, and software to manage user/source/outcome analyst workflow as the service provisioning line is complied with by the user.

The provisioning controller 204 has several interfaces, specifically, an access interface 228 to the central server 112 to store user information, a PMS interface to the user management system 108 and an assessment interface 224 that retrieves any assessment results, scans and other gathered results, which can include medical results. There are regimen trees 236 stored that are assigned to different user vectors. A user is tested to determine their user vector at a given point in time. The regimen trees 236 are designed with different service provisioning line state models that are used to improve the health of a user.

Different service locations can support different service provisioning lines such that the corresponding service provisioning modules can be selectively loaded to tailor an instance of the multimodal provisioning engine 104 uniquely for the service location as defined in a corresponding service location model 232. The service location model 232 defines the service provisioning lines supported and any special customizations for a particular service location. For example, a particular service location may support a chiropractic service provisioning module 212 that is customized to have three service sources such as physicians and the service location module would note the three sources to work in parallel such that scheduling is performed in that manner.

A service provisioning status system 208 manages scheduling interfaces with a provider status engine 220 and resource schedule database 216. The provider status system receives schedule information from all the different sources who are available for the service provisioning lines. The actual schedules can be stored on source devices 136 so that other calendar items can be coordinated. The resource schedule database 216 manages equipment, resources, rooms, classes, group sessions, etc.

Prediction models 224 are used to predict a value associated with provisioned services associated with achievement of a desired outcome, which desired outcome can, in some embodiments, be determined based on one or several attributes of the characterization-vector. Once a user vector is determined and mapped to a regimen tree, the prediction models 224 can be used to predict this value. As the outcome analyst updates progression along with the automatically gathered information, the user vector is updated along with the value prediction. In some embodiments, service provisioning can involve switching to different regimen trees which affects the prediction model. The prediction model 224 can apply learning algorithms to determine how a particular service location will progress a particular user through various regimen trees to determine value to achieve a target user composite characterization.

Figure 7:
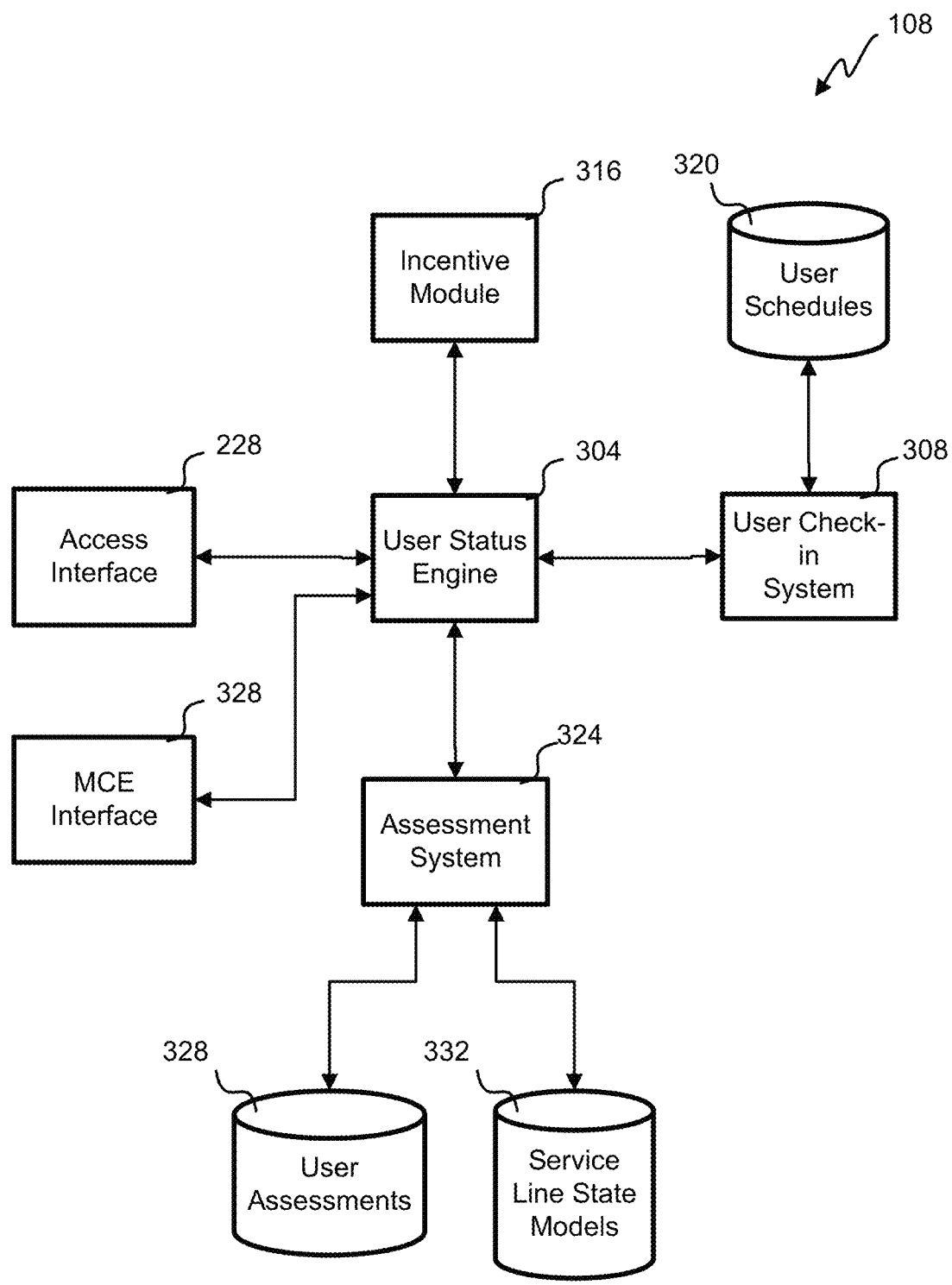
FIG. 7 is an illustration of one embodiment of a user management system.

With reference to FIG. 7, an embodiment of a user management system 108 is shown. The user management system 108 uses an access interface 228 to access a user profile database 116 and a MCE interface 328 to connect with the multimodal provisioning engine 104. A user status engine 304 manages user appointments and check-in along with assessment and incentives. A user check-in system 308 is coupled to user devices 140 to allow check-in remote from the service location. Surveys, data gathering, testing can be performed with the user device 140 before arriving at the service location. The user device 140 connects through the user portal 132 over the internet 124 to the user management system 108. Schedule information from the user device is stored in the user schedules database 320. Reconciliation is done by the user portal 132 at the time of scheduling or periodically to allow coordination with the service location.

An assessment system 324 determines compliance and progression of each user's wellness. User vectors, summary vectors and global health composites are all stored in the user assessment database 328. The assessment system 324 processes information gathered from wearables, manually entered by users/outcome analysts/sources, compliance with service provisioning line state models 332, clinical test results, etc. Generally, the assessment system 324 determines the fields for the user vector and processes that into summary vectors. For example, a field in the summary vector could be a function of several fields in the user vector. A global health composite is determined from the summary vector. The progress through the user's regimen trees 236 and service provisioning line state models 332 is tracked by the assessment system 324.

An incentive module 316 is used in the service provisioning line state models to encourage recovery and participation. For some user vectors, offering rewards or other encouragement by the incentive module is used to improve recovery. This gamification is controlled by the incentive module 316 to change the enticement in real time as the user vector evolves. Service provisioning can be resource intensive and the predictor models 224 allow estimating of these resources.

Figure 8:
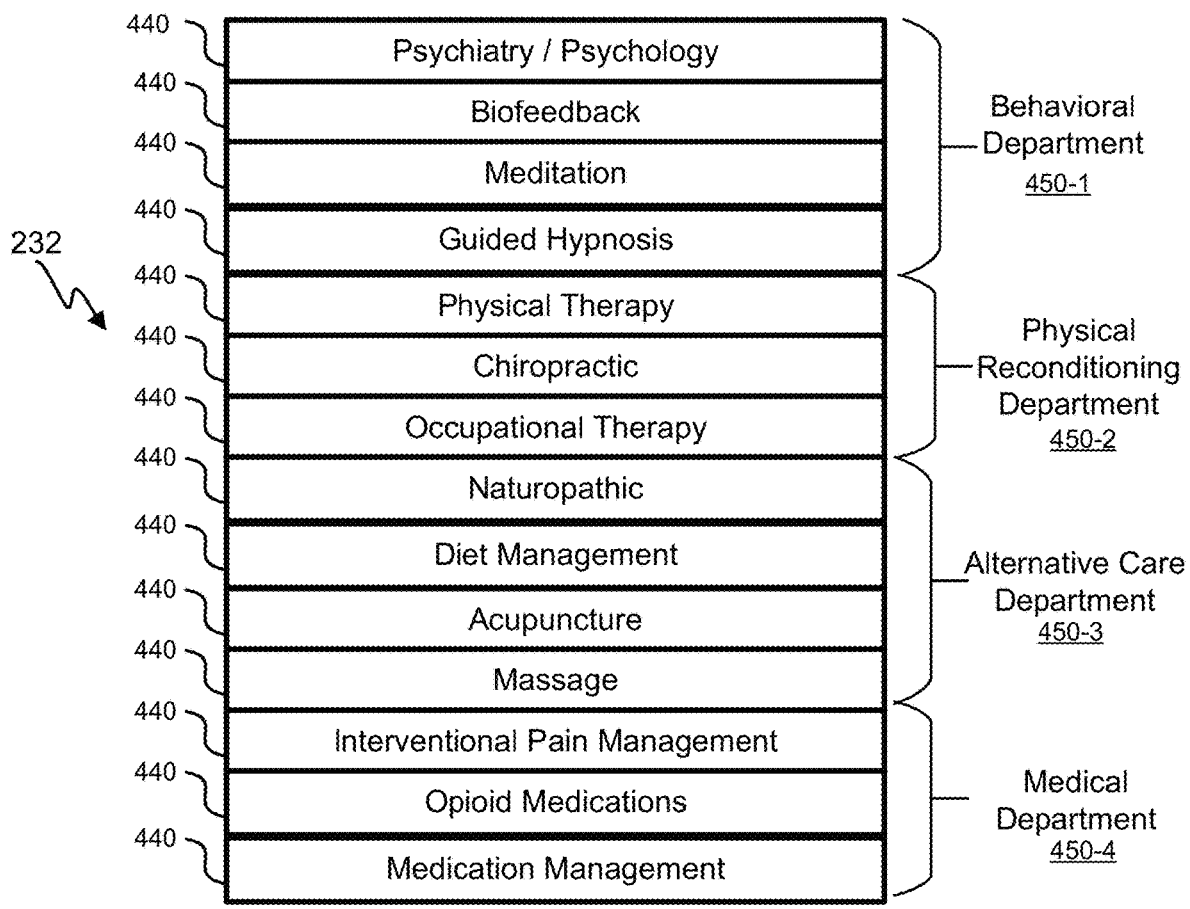
FIG. 8 is a schematic illustration of one embodiment of a service location model.

Referring next to FIG. 8, an embodiment of a service location model 232 is shown for an example service location. Different service provisioning lines 440 are organized into four departments 450, also referred to herein as four service groups 450. In some embodiments these service groups are formed based on one or several attributes of the service provisioning lines in the services groups, and in some embodiments, these service groups are formed independent of attributes of service providers provider these service lines. For example, the behavioral service group 450-1 includes the following service provisioning lines 440: psychiatry/psychology, biofeedback, meditation, and guided hypnosis. Different service locations have different service provisioning lines 440 and departments. Some service provisioning lines 440 can be outsourced so long as the corresponding service provisioning modules 212 are interacted with so that the service provisioning line state models 332 for each user are maintained such that the assessment system 324 can accurately track progress.

Figure 9:
FIG. 9 is an illustration of one embodiment of a plurality of service provisioning lines.

With reference to FIG. 9, an embodiment of the service provisioning lines 440 for a particular regimen 500 example is shown. The user vector can be mapped to a track and/or regimen tree that can include the following service provisioning lines 440: meditation, interventional pain management, chiropractic, and massage. The service provisioning lines 440 are dynamically selected for each user to interact with according the service provisioning line state model 332 for each of the service provisioning lines 440 assigned. Periodically, the regimen 500 is rearranged to include different service provisioning lines 440 relevant for the evolving condition of a user. For example, after six weeks the track is reconsidered to possibly change tracks and the service provisioning lines 440 associated therewith. In various embodiments, the length of time on a track before reconsidering can be a different amount or even change according to the progression of the user or available resources at the service location.

Figure 10:
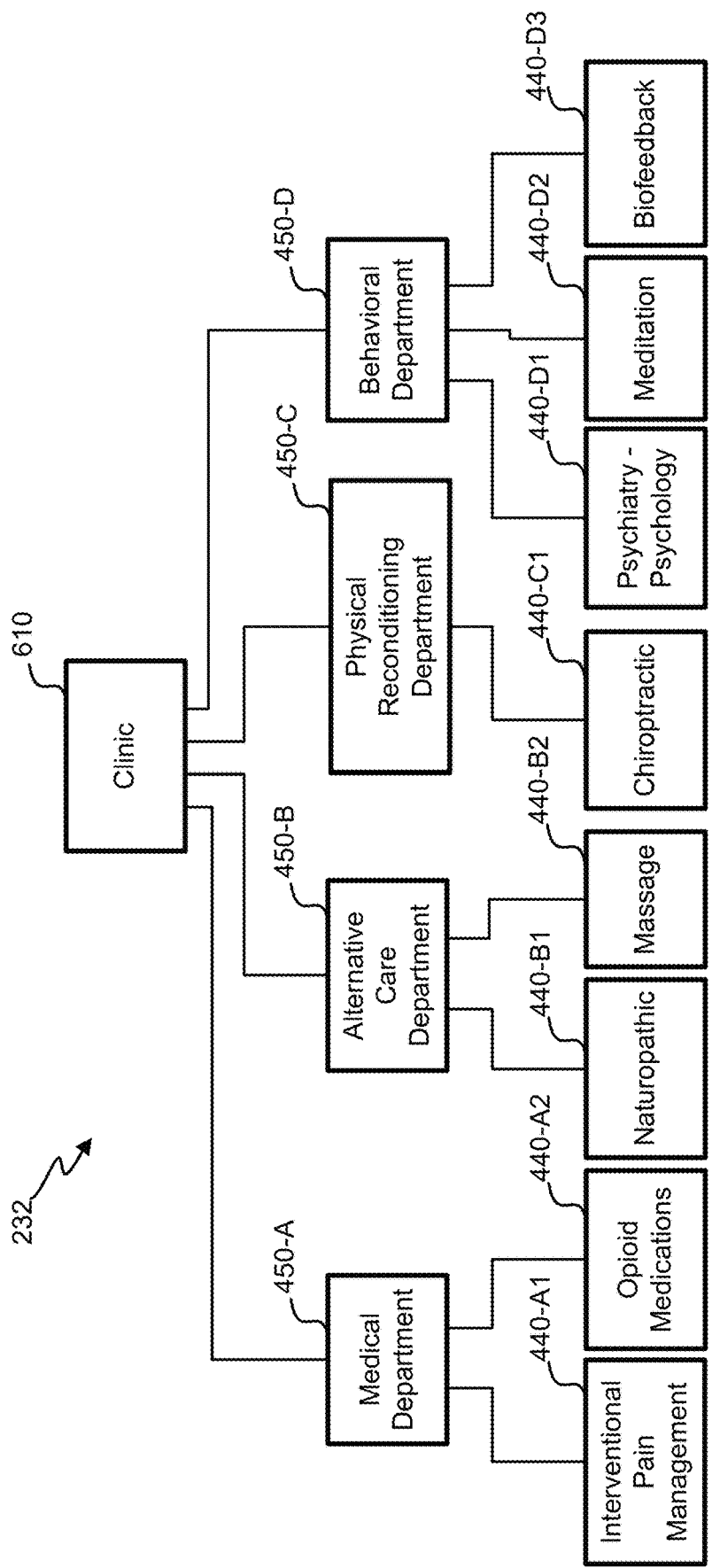
FIG. 10 is a schematic illustration of an embodiment of a service location.

Referring next to FIG. 10, an embodiment of a service location 232 is shown. This service location 610 has fewer service provisioning lines 440 than the embodiment of FIG. 4. For a particular regimen 500, service provisioning lines 440 available dictate those assigned. For example, if a service location did not have biofeedback 440-D3, meditation 440-D2 might be substituted instead. The service provisioning line state model 332 might be tweaked when there is a substitute to more fully serve as an equivalent.

Figures 11, 12, 13:
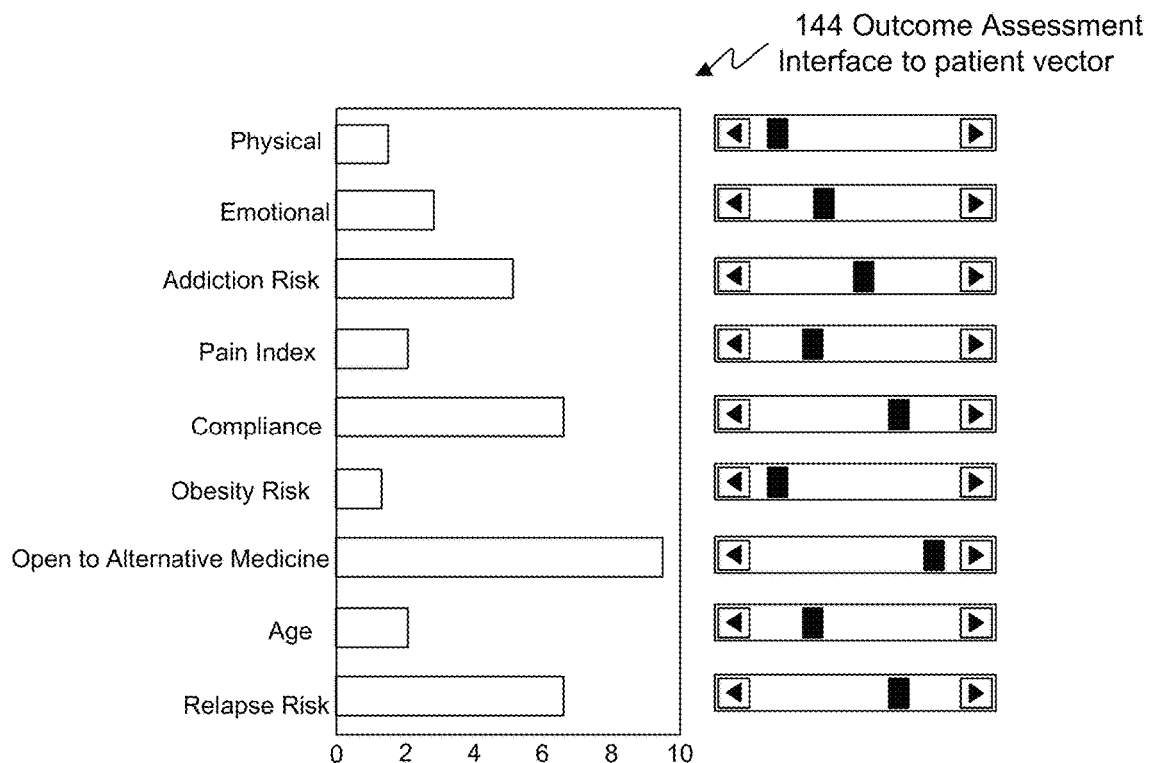
FIG. 11 is an illustration of one embodiment of an outcome assessment interface.
FIG. 12 is an illustration of one embodiment of a summary vector.
FIG. 13 is an illustration of one embodiment of an emotional versus physical matrix.

With reference to FIG. 11, an embodiment of an outcome assessment interface 144 is shown. The outcome analyst interacts with the outcome assessment interface 144 to review the scoring of the various fields of the user vector. This embodiment allows the outcome analyst to override the scoring according to updated testing, clinical results, etc. Some embodiments allow sources to modify fields of the user vector. In this embodiment, there are nine fields in user vector that are measured, but other embodiments can have more or less fields.

Referring next to FIG. 12, an embodiment of a summary vector 700 is shown. In this embodiment, the nine fields in user vector are simplified into a four field summary vector 700. The fields of the summary vector are a function of the fields in the user vector and optionally other information. For example, the fields for addiction risk, pain index and relapse risk can be summarized as opiate risk 816 in the summary vector 700. Various fields from the user vector might be normalized or otherwise processed such that the field in the summary vector 700 is a function of those value from the user vector. For example, opiate risk might be addiction risk plus the pain index and relapse risk, but scaled according to the dosage of their opiate prescription.

With reference to FIG. 13, an exemplary embodiment of an emotional versus physical matrix 800. The physical field 804 and emotional field 812 from the summary vector 700 are mapped in a three by three matrix according to each of those fields being in three intensities, specifically, mild, moderate and severe. Users are grouped in these coarse categories to simplify their handling in one of three tracks. The emotional track is for users assigned to cells 1B, 1C and 2C. The physical track is for is for users assigned to cells 2A, 3A and 3B. For users in between those two diagnosis, a mixed track lies in the middle with users assigned to cells 1A, 2B and 3C. When sources are reviewing users, the assigned cell is shorthand for their condition as the full user vector is difficult to remember the relevance of each field.

Figure 14:
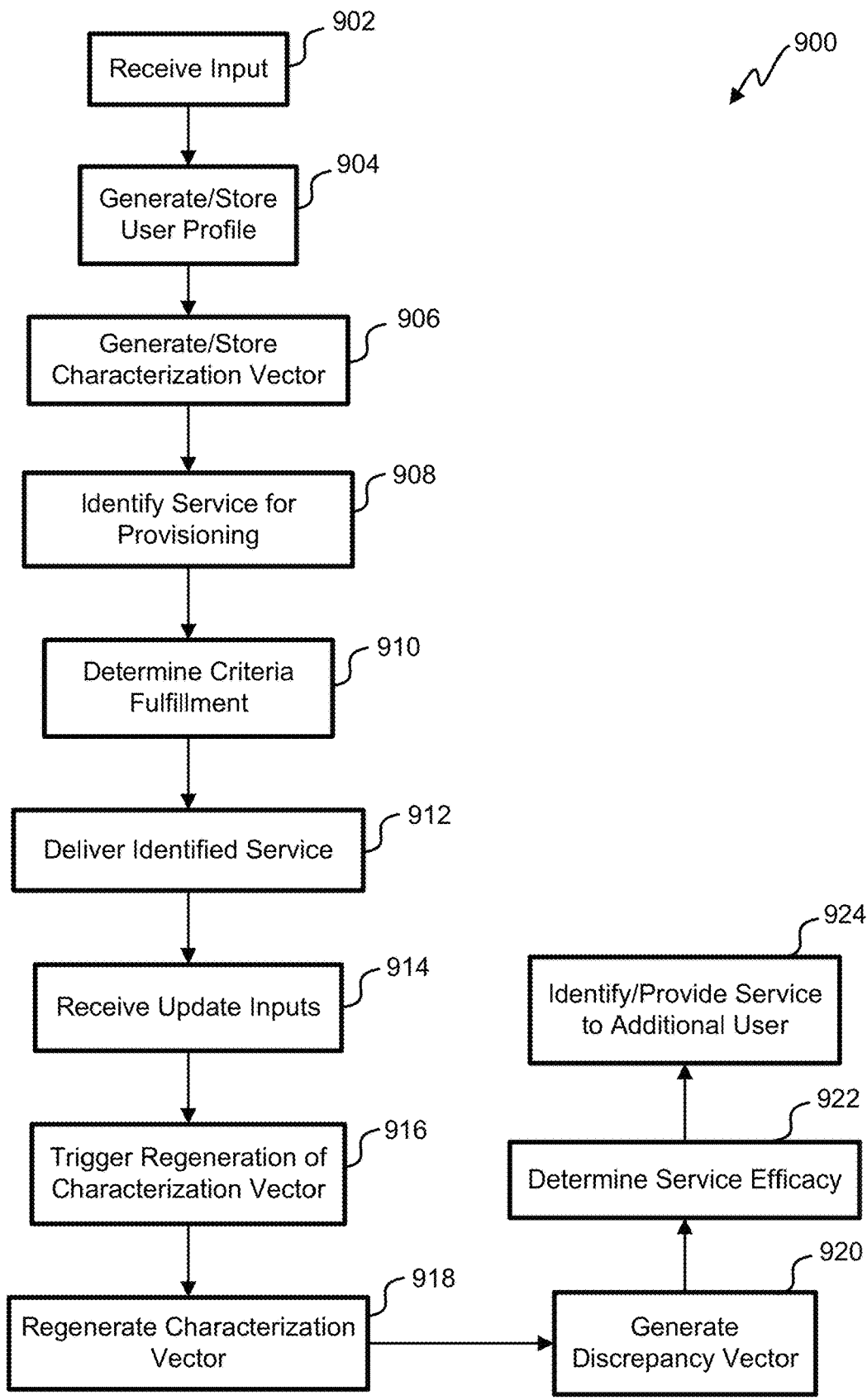
FIG. 14 is a flowchart illustrating one embodiment of a process for automated characterization-vector based prediction.

With reference now to FIG. 14, a flowchart illustrating one embodiment of a process 900 for automated characterization-vector based prediction is shown. The process 900 can be performed by all or portions of the automated provisioning network 10 including, for example, all or portions of the multimodal provisioning system 100. The process 900 begins a block 902 wherein one or several inputs are received. In some embodiments, each of these one or several inputs can be received from one or several devices 136, 140, 141, 148. In some embodiments, the inputs can be received by the central server 112, and in some embodiments, some or all of these inputs can relate to a single subject-user.

After the input has been received, the process 900 proceeds to block 904, wherein the user profile is generated, updated, and/or stored based on the received inputs. In some embodiments, the user profile can be generated and/or updated by the central server 112 and can be stored in the user profile database 116. The user profile can relate to the single subject-user for whom some or all of the inputs in block 902 were received. In some embodiments, the user profile identifies n-dimension attributes of the single subject-user for whom some or all of the inputs in block 902 were received. In some embodiments, the single subject-user, is referred to as a first subject-user.

At block 906, a characterization vector can be generated and/or stored. The characterization vector can be generated by the central server 112 from all or portions of the user profile, and in some embodiments, the characterization vector can be stored in the user profile database 116. In some embodiments, the characterization vector can comprise a plurality of dimensions, each of which can comprise a gradated classification indicator. In one embodiment, for example, the characterization vector can comprise four dimensions, each of which four dimensions can comprise a gradated classification indicator. In one embodiment, for example, the four dimensions can comprise, a physical dimension, and emotional dimension, and interaction dimension, and a vulnerability dimension.

In some embodiments, the physical dimension can characterize all or portions of the physical state of the subject-user, the emotional dimension can characterize all or portions of the emotional state of the subject-user, the interaction dimension can characterize all or portions of the subject-users social interactions, and the vulnerability dimension can characterize all or portions of the subject-users social vulnerability. In some embodiments, the physical dimension can be characterized by a gradated classification indicator which can be expressed as, for example, one of the numerals: 1, 2, or 3, and in some embodiments, the emotional dimension can be characterized by a gradated classification indicator which can be expressed as, for example, one of the letters: A, B, or C. In some embodiments, the interaction dimension can have two sub-dimensions including, interactions with oneself and interactions with others. The sub dimension relating to interactions with oneself can attempt to classify motivation levels of the subject-user, and can be characterized by a gradated classification indicator which can be expressed as one of the colors: green, yellow, or red. The sub-dimension relating to interactions with others can attempt to classify the subject-user's response to interactions with others and the sub dimension can be characterized by a gradated classification indicator which can be expressed as one of the shapes: circle, square, or triangle. The vulnerability dimension can be characterized by a gradated classification indicator which can be expressed as one of the levels: low, medium, or high.

After the characterization vector has been generated, the process 900 proceeds to block 908 wherein a service is identified for provisioning. In some embodiments, the service for provisioning can be identified according to an artificial intelligence (AI) machine-learning model. In some embodiments, this machine-learning model can be trained to output a service for provisioning and/or a service intensity based on the input of the characterization vector, based on the input of portions of the characterization vector, and/or based on the input of portions of the user profile. In some embodiments, and as a part of the identifying of the service for provisioning, the server 112 can be configured to ingest at least a portion of the characterization vector into the AI machine-learning model.

In some embodiments, the service identified for provisioning can comprise a digital component and a non-digital component. In some embodiments, the service for provisioning can be identified according to the characterization vector including, for example, according to all or portions of the magnitude, and/or direction of the characterization vector. In some embodiments, all or portions of the characterization vector can be linked to one or several services or actions in the action database 117. In some embodiments, this link can be to one or several services or actions can be via edges and corresponding conditional probabilities characterizing the strength of the link with those services, and/or actions. In some embodiments, the digital component, can comprise content for delivery to the subject-user. This content can comprise one or several videos, messages, texts, text strings, emails, or the like. In some embodiments, the digital component can comprise one or several reminders, one or several calendar entries, one or several videos, or the like. In some embodiments, the non-digital component, can comprise one or several tests, clinic visits, scans, evaluations, therapies, surgeries, treatments, medications, or the like. In some embodiments, the service for provisioning can be identified by querying the action database 117 for a service based on attributes of the user. In some embodiments, these attributes can be embodied by the characterization vector. In response to this request, the action database 117 can provide identification of one or several services or actions.

At block 910, a delivery criteria is identified and the fulfillment status of that delivery criteria is determined. In some embodiments, for example, the delivery criteria can identify one or several parameters constraining delivery of the identified service. These can be, for example, one or several times, or location parameters, which time, or location parameters can specify a timeframe in which the service can be delivered and/or a location in which the service can be delivered. In some embodiments, the delivery criteria can relate to the digital component of the service and/or to the non-digital component of the service. In one embodiment, for example, the delivery criteria can comprise one or several conditions for fulfillment before the digital component of the service can be provided. These conditions can include, for example, an amount of elapsed time since the receipt of the input in block 902. In some embodiments, the determination of fulfillment of the delivery criteria can be made based on information and/or data contained in the data stream outputted by the messaging bus 56. In some embodiments, for example, data contained in the data stream received from the messaging bus 56 can indicate the completion of an event corresponding to the fulfillment of the delivery criteria.

At block 912, the service identified in block 908 is delivered. In some embodiments, the delivery of this service can include the automatic delivery of the digital component of the service subsequent to the automated determination of the fulfillment of at least one delivery criteria. In some embodiments, the identified service can be delivered based on data contained in the data stream received from the messaging bus 56, which information contained in the data stream of the messaging bus 56 can serve as a trigger for delivery of the service and/or of the service component. As discussed above with respect to block 910. In some embodiments, the identified service can be delivered through the multimodal system 100, and/or via a source associated with and/or using the multimodal system 100.

After the identified service has been delivered, the process 900 proceeds to block 914, wherein one or several updates are received. In some embodiments, these updates can be update inputs which can be received and a similar manner to the inputs received in block 902 discussed above. In some embodiments, these updates can correspond to updates for at least some of the n-dimension attributes of the first-user, and in some embodiments, these updates can be received from the source device 136.

After the updates have been received, the process 900 proceeds to block 916, wherein regeneration of the characterization is triggered. In some embodiments, the regeneration of the characterization vector can be triggered when a predetermined amount of updates have been received, when a predetermined time period has passed, and/or based on the received input requesting regeneration of the characterization vector. After the regeneration of the characterization vector has been triggered, the process 900 proceeds to block 918, wherein the characterization vector is regenerated. In some embodiments, the characterization vector can be regenerated from the n-dimension attributes of the first user. In some embodiments, these n-dimension attributes can include the update to some of the n-dimension attributes of the first user. In some embodiments, the regeneration of the characterization vector can be performed in a similar manner to the generation of the characterization vector discussed in block 906.

After the characterization vector has been regenerated, the process 900 proceeds to block 920 wherein user progress is determined. In some embodiments, user progress can be determined by a comparison of the characterization vector generated in block 906 to the regenerated characterization vector. In some embodiments, and as a part of this comparison, a discrepancy vector can be generated, which discrepancy vector can characterize the difference between the characterization vector generated in block 906. In the regenerated characterization vector.

In some embodiments, after the determination of user progress, the process 900 can proceed to block 922 wherein an efficacy of the service is determined. In some embodiments, this efficacy can be determined based on the comparison of block 920, and specifically based on the discrepancy vector. In some embodiments, the determined efficacy can be used to update all or portions of the action database 117, including, for example, the conditional probabilities blinking actions and/or services, to all or portions of the characterization vector of the first-user.

As indicated at block 924, in some embodiments, services can be identified for provisioning to additional subject-users during or after the completion of some or all of steps 902 through 922. In some embodiments, the identifying and/or provisioning of services, to one or several additional subject-users can include, for example, the receipt of inputs relating to a second subject-user, the generating and/or storing of a profile for the second subject-user, the generating of a characterization vector for the second subject-user, the identifying of one or several services for provisioning to the second subject-user, and/or the delivery of those identified services to the second subject-user. In some embodiments, services for the second subject-user can be identified based on the determined efficacy of the services provision to the first subject-user, and specifically according to updates to the action database 117, subsequent to the determination of efficacy of services indicated in block 922.

Figure 15:
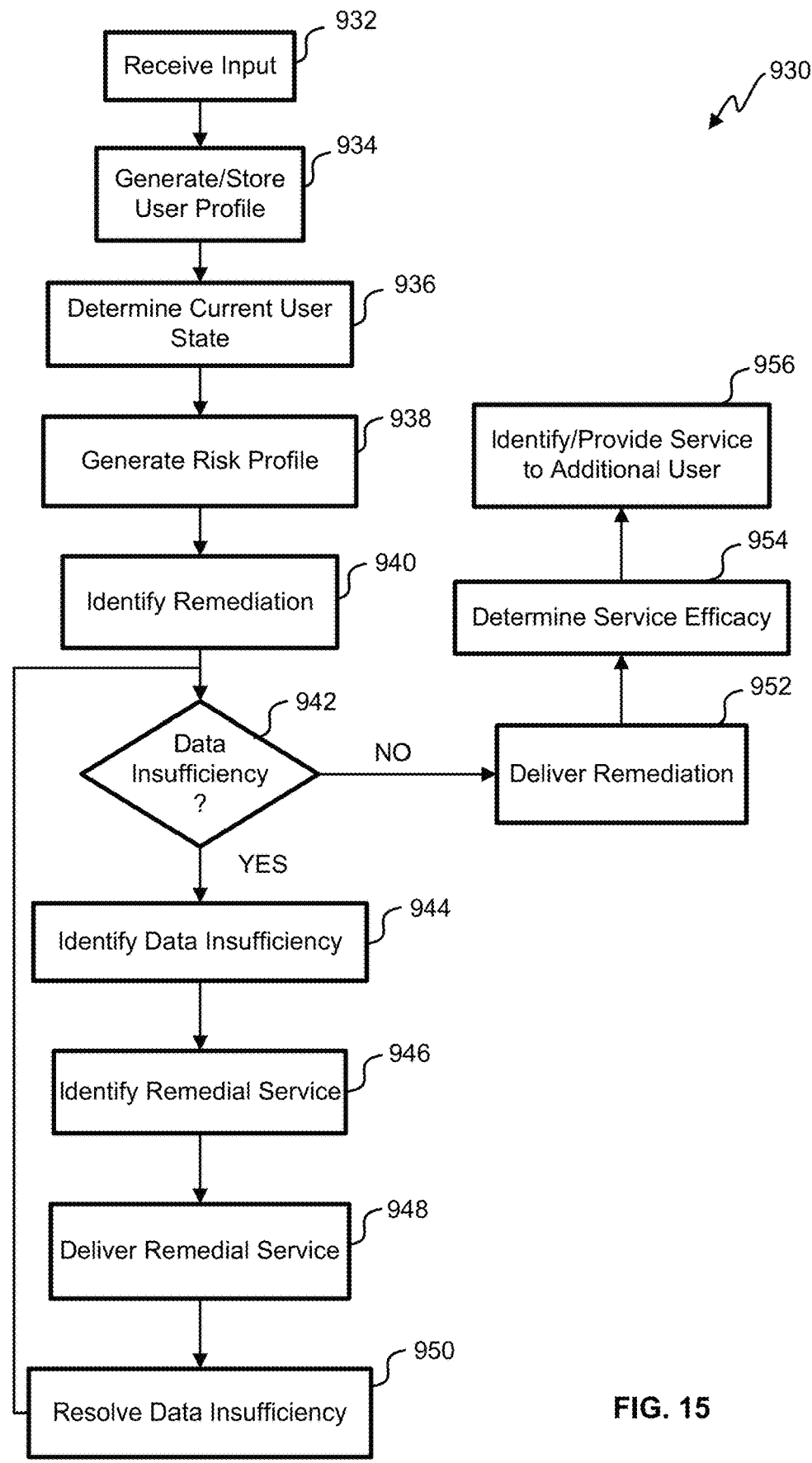
FIG. 15 is a flowchart illustrating one embodiment of a process for multimodal remediation.

With reference now to FIG. 15, a flowchart illustrating one embodiment of a process 930 for multimodal remediation is shown. The process 930 can be performed by all or portions of the automated provisioning network 10 including, for example, all or portions of the multimodal provisioning system 100. The process 930 begins a block 932 wherein one or several inputs are received. In some embodiments, each of these one or several inputs can be received from one or several devices 136, 140, 141, 148. In some embodiments, the inputs can be received by the central server 112, and in some embodiments, some or all of these inputs can relate to a single subject-user.

After the input has been received, the process 900 proceeds to block 904, wherein the user profile is generated, updated, and/or stored based on the received inputs. In some embodiments, the user profile can be generated and/or updated by the central server 112 and can be stored in the user profile database 116. The user profile can relate to the single subject-user for whom some or all of the inputs in block 902 were received. In some embodiments, the user profile identifies n-dimension attributes of the single subject-user for whom some or all of the inputs in block 902 were received. In some embodiments, the single subject-user, is referred to as a first subject-user.

At block 936, a current state of the subject-user is determined. In some embodiments, the current state of the user can be determined according to all or portions of the user profile and/or according to the characterization vector can be generated according to block 906 of FIG. 14. The current state of the subject-user can be determined by the central server 112.

After the current state of the subject-user is determined, the process 930 proceeds to block 938, wherein a risk profile is generated for the subject-user. In some embodiments, the risk profile can be generated according to the current state of the subject-user by, for example, the central server 112. The risk profile can identify and/or characterize a likelihood of an adverse outcome to the subject-user. The risk profile can be generated according to a machine learning model that receives user attributes as inputs and outputs a risk profile which can include a level of risk, and events associated with that risk level. In some embodiments, the risk profile can identify and/or characterize a likelihood of an adverse outcome to the subject-user within a common, for example, predetermined timeframe.

After the risk profile has been generated, the process 930 proceeds block 940, wherein a remediation is identified. In some embodiments, the remediation can correspond to the service identified in block 908 of FIG. 14. In some embodiments, this remediation can be identified via, for example, an AI machine-learning model, and this remediation has been identified and/or selected to mitigate the likelihood of the adverse outcome. In some embodiments, the remediation can be identified based on user profile and/or the current state of the subject-user. The remediation can be identified by the central server 112.

After the remediation has been identified, the process 930 proceeds to decision state 942 wherein it is determined if there is a data insufficiency for the subject-user. In some embodiments, this data insufficiency can comprise one or several missing attributes of the subject-user. In some embodiments, this data insufficiency can prevent, for example, at least one of the completing of the determination of the current state of the subject-user, the completing of the generation of the risk profile, and/or the completing of identification of the remediation. In some embodiments, for example, this data insufficiency may not prevent the determination of the current state of the subject-user, the generation of the risk profile, and/or the identification of the remediation, but this data insufficiency may prevent the performing of these steps at a desired confidence level, and/or accuracy level. In some embodiments, the data insufficiency can be evaluated by the server 112.

If it is determined that there is a data insufficiency, then the process 930 proceeds to block 944, wherein the data insufficiency is identified. After the data insufficiency has been identified, the process 930 proceeds to block 946 wherein a remedial service is identified. In some embodiments, the remedial service can be a service for provisioning to the first user and/or to the subject-user, which service is identified to remedy the data insufficiency. In some embodiments, this service can comprise a digital component, and/or a non-digital component. In some embodiments, the digital component can comprise a plurality of timed and/or automatically triggered reminders. In some embodiments, some or all of these reminders can direct the subject-user to complete an action, which action can be associated with the non-digital component of the service. In some embodiments, the remedial service can be identified by the server 112 identifying attributes of the missing data giving rise to the data insufficiency and identifying services through which data corresponding to those attributes is generated and/or determined.

After the remedial service has been identified, the process 930 proceeds to block 948, wherein the remedial service is delivered. In some embodiments, this can include delivery of the digital component of the service, and/or of the non-digital component. In some embodiments, the digital component can be automatically delivered, and specifically can be automatically delivered subsequent to the automated determination of fulfillment of at least one delivery criteria as discussed in greater detail with respect to block 910 and 912 of FIG. 14.

After the remedial service has been delivered, the process 930 proceeds to block 950, wherein the data insufficiency is resolved. In some embodiments, this can include the updating of the user profile with inputs generated from the delivery of the remedial service and/or with inputs generated subsequent to delivery of the remedial service. In some embodiments, and as part of the resolving of the data insufficiency, the previously uncompleted one or more of: determination of the current state of the subject-user, generation of the risk profile of the subject-user, and/or identification of the remediation, is completed.

After the data insufficiency has been resolved, the process 930 returns to decision state 942 wherein it is determined if the data insufficiency still exists. If it is determined that there is no data insufficiency, then the process 930 proceeds to block 952 wherein the remediation is delivered. After the remediation has been delivered, the efficacy of the remediation can be determined and block 954. In some embodiments, the efficacy can be determined similar to the determination block 922 of FIG. 14.

As indicated at block 956, in some embodiments, services can be identified for provisioning to additional subject-users during or after the completion of some or all of steps 932 through 954. In some embodiments, the identifying and/or provisioning of services, to one or several additional subject-users can include, for example, the receipt of inputs relating to a second subject-user, the generating and/or storing of a profile for the second subject-user, the generating of a characterization vector for the second subject-user, the identifying of one or several services for provisioning to the second subject-user, and/or the delivery of those identified services to the second subject-user. In some embodiments, services for the second subject-user can be identified based on the determined efficacy of the services provisioned to the first subject-user, and specifically according to updates to the action database 117 subsequent to the determination of efficacy of services indicated in block 954.

Figure 16:
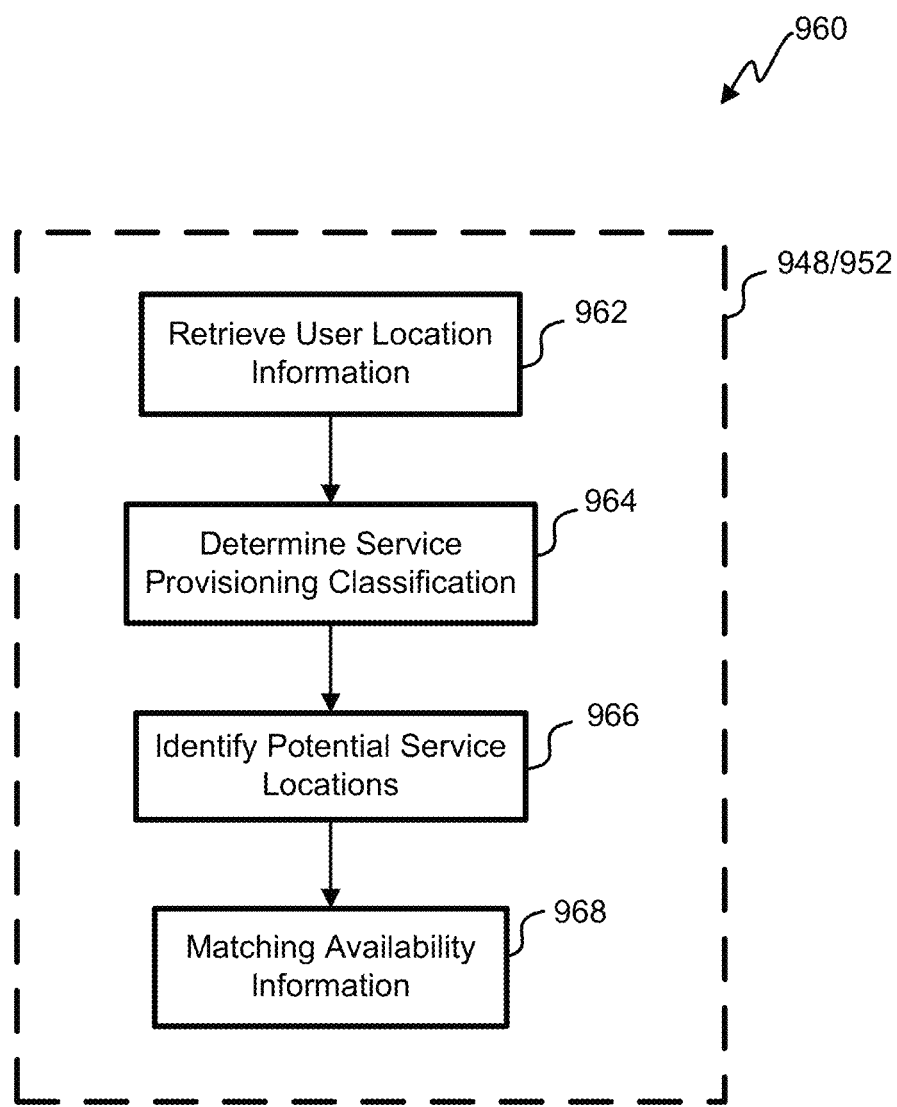
FIG. 16 is a flowchart illustrating one embodiment of a process for scheduling of service provisioning.

With reference now to FIG. 16, a flowchart illustrating one embodiment of a process 960 for scheduling, and specifically for automatic scheduling of service provisioning is shown. In some embodiments, the process 960 can be performed as a part of, or in the place of one or both of steps 948, 952. The process 960 begins at block 962, wherein user location information is retrieved. In some embodiments, this can include current location information and/or location history information. In some embodiments, the location history information can identify user location information over a past period of time, and in some embodiments, the location history information can identify historic trends in the user location and/or the user movement. This can include identifying locations the user regularly frequents at certain times, travel routes, normal times of travel, or the like. The location information can be retrieved from the user device 140 and/or from the user profile database 116.

After the location information is retrieved, the process 960 proceeds to block 964, wherein service provisioning classification is determined. In some embodiments, this can include determining classification of the service for provisioning, and specifically determining one or several attributes of the service for provisioning. In some embodiments, this classification can identify one or several attributes of the service location from which the service can be received. These attributes can specify, for example, the type of location such as, for example, a hospital, surgical center, a clinic, or the like. In some embodiments, this information can be retrieved from the action database 117.

After the service provisioning classification has been determined, the process 960 proceeds to block 966 wherein potential service locations are determined. In some embodiments, these potential service locations are determined based on a combination of the location of potential service locations, user location information, service classification, and/or service location attributes. In some embodiments, the service location attributes can identify one or several service types provided at a service location. In some embodiments, the identification of potential service locations can include identifying one or several service locations that are conveniently located with respect to the user location history and that provide services corresponding to the remedial service and/or to the remediation.

After potential service locations of an identified, the process 960 proceeds to block 968 wherein availability information for the user, as was for the potential service locations is identified and unmatched. In some embodiments, this can include matching the schedule of the subject-user to the schedule of sources at the service location. In some embodiments, this can further include matching the schedule of the subject-user when the subject-user is close to one of the potential service locations to the schedule of sources at that one of the potential service locations. This matching can be performed by the central server 112.

Figure 17:
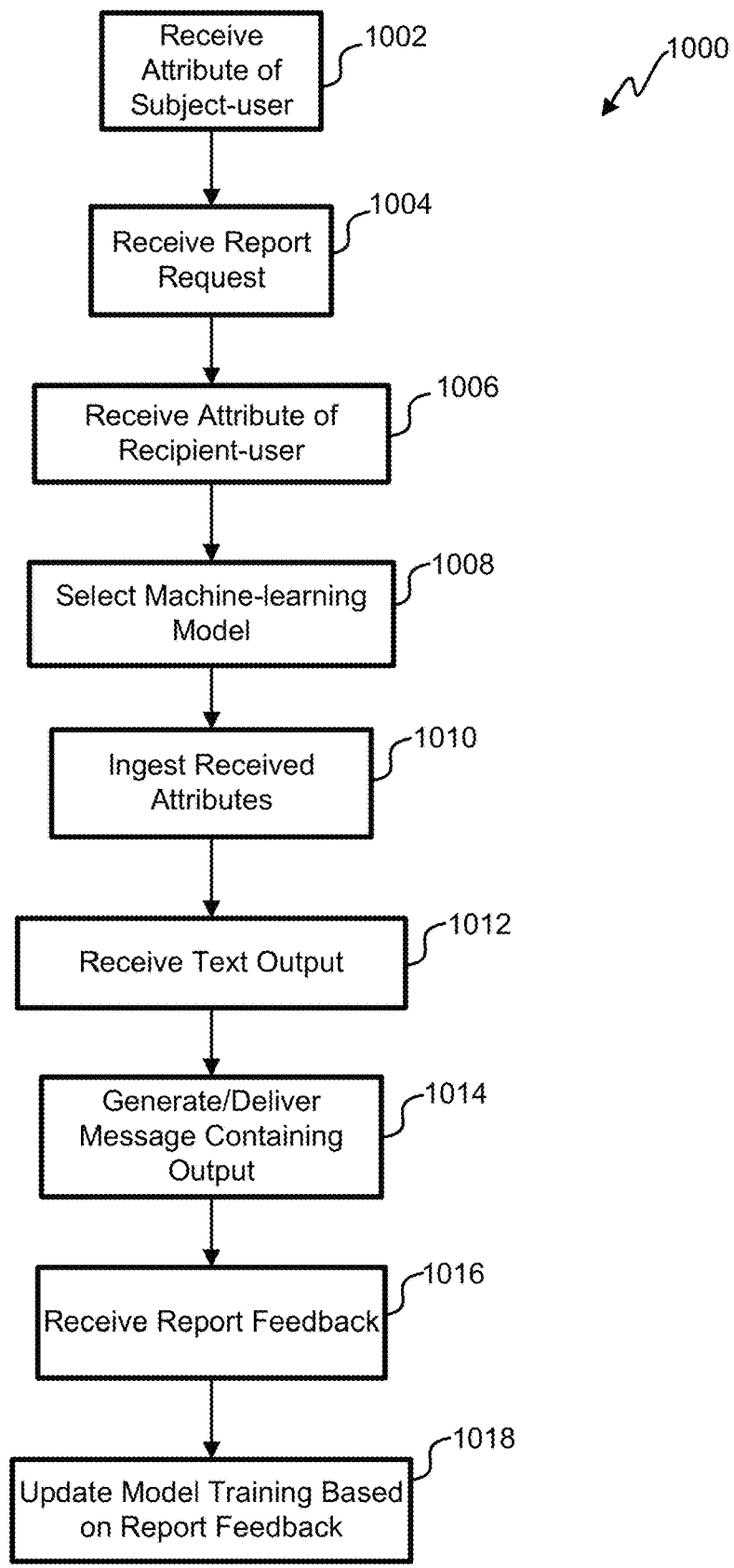
FIG. 17 is a flowchart illustrating one embodiment of a process for automatic customized output generation delivery.

With reference now to FIG. 17, a flowchart illustrating one embodiment of a process 1000 for automatic customized output generation delivery is shown. The process 1000 can be performed by all or portions of the automated provisioning network 10 including, for example, all or portions of the multimodal provisioning system 100. The process 1000 begins at block 1002, wherein an attribute of the subject-user is received. In some embodiments, the attribute of the subject-user can be received from one of the devices 136, 140, 141, 148. In some embodiments, this attribute can be generated and/or provided based on a provided service, based on an input from the subject-user to the user device 140, and/or from a source to the provider device 136. In some embodiments, this attribute can be received from testing equipment such as from medical testing equipment. In some embodiments, this medical testing equipment, also referred to herein as an electrical analysis machine, generates data indicative of the attribute of the subject-user from an interaction with the subject-user. In some embodiments, the electrical analysis machine automatically provides the data indicative of the attribute of the subject-user to the server 112.

In some embodiments, at least some of the attributes of the subject-user can be received form the source device 136. In some embodiments, for example, the attribute can characterize a clinical visit, treatment, medication, procedure, diagnosis, or the like, provided to or for the subject-user. After the attribute of the subject-user has been received, the attribute can be stored in the user profile database 116 and can be, in some embodiments, added to the user profile.

At block 1004, a report request is received by the server 112. This report request can include information identifying an attribute of the recipient-user. In some embodiments, the report request can be received by the server 112 from one of the devices 136, 140, 141, 148. In some embodiments, the report request can be received from a recipient device 141, which recipient device can be any device used by any class of user to request a report from the multimodal provisioning system 100 and/or from the automated provisioning network 10. In some embodiments, users of the multimodal provisioning system 100 and/or from the automated provisioning network 10 can each belong to one or more of one or several classes. In some embodiments, these classes are fixed classes that are associated with the role of each user in providing services to the subject-user. Thus, in some embodiments, one class can be subject-users, one class can be sources, one class can be insurers, one class can be regulators, and/or one class can be administrators. In some embodiments, the classes can be customized based on attributes of users. In some embodiments, these classes can include at least one class of subject-users and at least two-classes of recipient-users. These attributes can include, for example, level of sophistication, information relating to degree of follow-up and/or requests for further information have been made by the user, or the like.

After the report request has been received, the process 1000 proceeds to block 1006, wherein attributes of the recipient-user are received. In some embodiments, these attributes of the recipient-user can be embedded in the report request and specifically can be embedded in metadata of the report request. In some embodiments, this attribute of the recipient-user can identify the one or several classes to which the recipient-user belongs, and/or the attribute can be used to identify the one or several classes to which the recipient-user belongs.

After the attribute of the recipient-user has been received, the process 1000 proceeds to block 1008, wherein a machine-learning model is selected. In some embodiments, the multimodal provisioning system 100 can include a model database 119, which model database 119 can be accessed by the server 112. The model database 119 can comprise a plurality of machine-learning models, which can be natural language generation models, that are trained to generate text. In some embodiments, these machine-learning models can be trained to generate text in response to inputs characterizing attributes of at least one subject-user and at least one recipient-user. In some embodiments, each of the classes of users can be associated with at least one of the machine-learning model such that when a class of recipient-user is identified, a corresponding machine-learning model can be identified. In some embodiments, the machine-learning model can be selected by comparing the class of the recipient-user to metadata associated with each of the machine-learning models. In some embodiments, the machine-learning model can be selected by querying the model database 119 for a model corresponding to the class of the recipient-user.

In some embodiments, the selecting of the machine-learning model can include the ingestion of the information into the machine-learning model as indicated in block 1010. In some embodiments, this information can comprise received attributes of the subject-user and/or attributes of the recipient-user. In some embodiments, for example, information resulting from a service provided to the subject-user can be ingested into the machine-learning model. In some embodiments, this ingestion can include the generation of a vector and/or tensor comprising the information relating to the subject-user and the inputting of the vector and/or tensor into the machine-learning model.

After ingesting the received attributes, the process 1000 proceeds to block 1012, wherein a text output is received from the machine-learning model. In some embodiments, the text output can from the machine-learning model can be the text generated by the machine learning model. In some embodiments, the text output can be customized to the recipient-user. After the output text is received, the process 1000 proceeds to block 1014, wherein a message containing the text output is generated and deliver. In some embodiments, the message can be generated and delivered by the server 112. The message can comprise at least portions of the text output of the machine-learning model. The message can be generated and/or sent by the communications subsystem 86 of the server 112.

After the message containing the output text has been generated and/or sent, the process 1000 proceeds to block 1016, wherein report feedback is received. In some embodiments, the report feedback can include information indicate whether and/or the degree to which the generated and/or delivered message responded to the report request of block 1004. In some embodiments, the report feedback can be received by the server 112 from the recipient device 141 from which the report request originated.

After the report request has been received, the process 1000 proceeds to block 1018, wherein the training of the machine-learning model used to generate the output text is updated. In some embodiments, this can include modifying aspects of the machine-learning model such as, for example, one or several weightings within the machine-learning model. In some embodiments, this modifying of the training of the machine-learning model can be automatically performed and/or the training of the machine-learning model can be updated based on the received report feedback.

Figure 18:
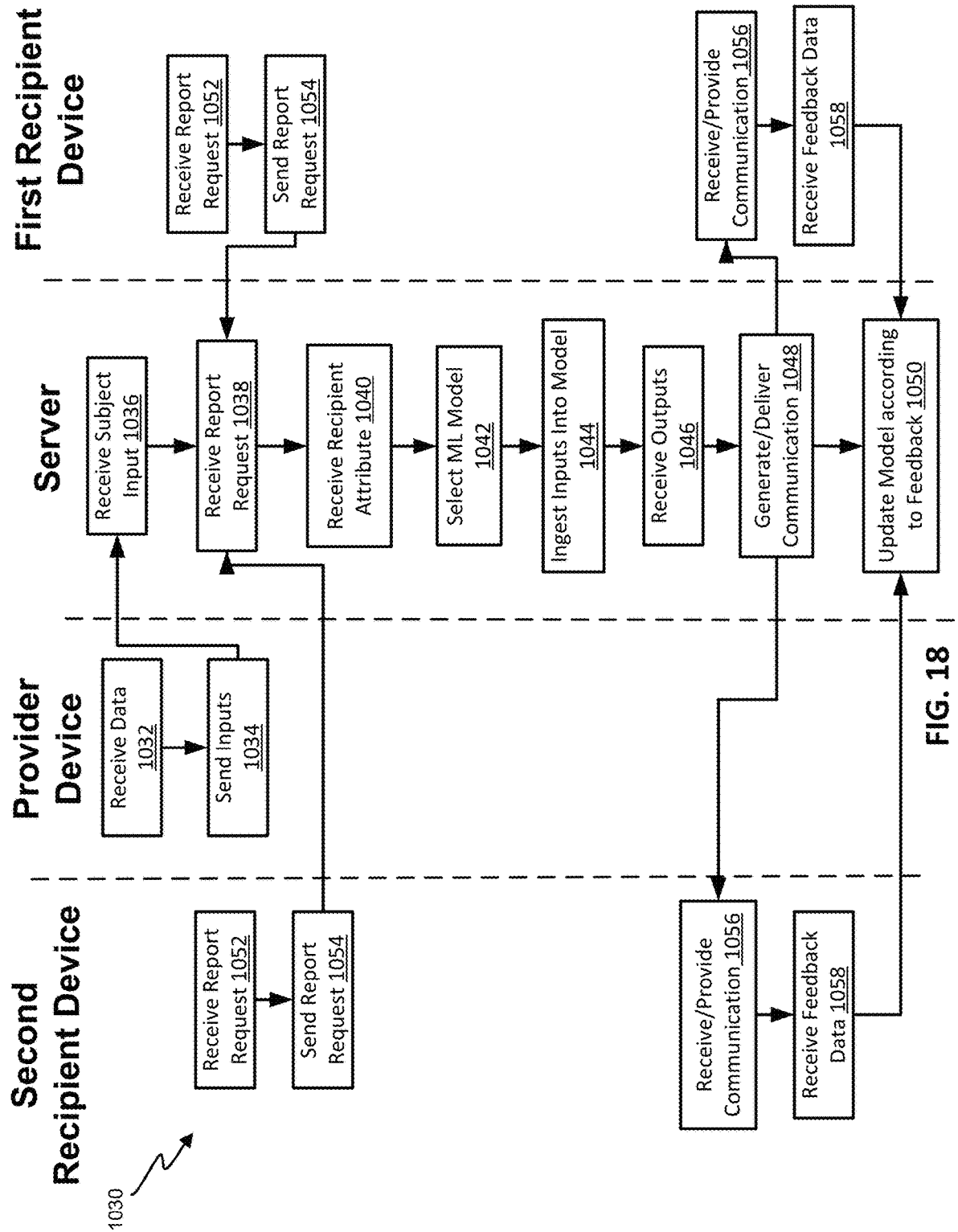
FIG. 18 is a swim lane diagram of one embodiment of a process for automatic customized output generation delivery.

With reference now to FIG. 18, a swim lane diagram of one embodiment of a process 1030 for automatic customized output generation delivery is shown. The process 1030 can be performed by all or portions of the automated provisioning network 10 including, for example, all or portions of the multimodal provisioning system 100. The process 1030 begins at block 1032, wherein data is received by a device, which can be the source device 136. In some embodiments, this data can characterize an attribute of the subject-user. This data can be converted into one or several communications and/or signals and send to the server 102 as indicated in block 1034.

At block 1036, the one or several communications sent in block 1034 are received by the server 112 in block 1036. In some embodiments, and as indicated in blocks 1052 and 1054, a report request can be received by a recipient device 141 and can be sent to the server 112 as indicated in block 1054. In some embodiments, a first report request can be received by a first recipient device 141 at a first time and a second report request can be received by a second recipient device 141 at a second time. At block 1038, one or several of these report requests can be received by the server 112 from one or more of the recipient devices 141. In one embodiment, a first report request can be received from a first recipient device 141 at a first time.

After the report request is received, the process 1030 proceeds to block 1040, wherein a recipient attribute is received. In some embodiments, this recipient attribute can identify a class of the recipient-user. In some embodiments, this recipient attribute can be received simultaneous with receipt of the report request. In one embodiment, for example, the recipient attribute can accompany the report request.

After the recipient attribute has been received, the process 1030 proceeds to block 1042, wherein a machine-learning model is selected based on the received recipient attribute. This machine-learning model can be selected from machine-learning models stored in the model database 119. After the machine-learning model has been selected, the process 1030 proceeds to block 1044, wherein inputs are ingested into the machine-learning model, which ingestion leads to the machine-learning model outputting text. These outputs are received in block 1046 by the server 112. In some embodiments, the outputting of text by the machine-learning model can be indicated in the data stream of the messaging bus 56.

In some embodiments, these one or several indicia of the outputting of the text can trigger the generation and delivery of a message to the recipient-user device 141 from which the report request was received.

In some embodiments, the generated and/or delivered message can be received by the recipient-user device 141 from which the report request was received. In response to the receipt of this communication, the recipient-user device receiving the message can receive feedback data from the recipient-user. In some embodiments, this feedback data can characterize the degree to which the communication is responsive to the report request. The feedback data can be provided to the server 112 from the recipient-user device 141, and this data can be used to update the machine-learning model.

In some embodiments, a second report request can be received by the server 112 from a second recipient-user device 141. The second report request can comprise at least one input identifying an attribute of the second recipient-user. In some embodiments, the attribute of the second recipient-user is different than the attribute of the first recipient-user. In some embodiments, this different attribute can result in the second recipient-user having a different class than the first recipient-user.

In some embodiments, and after receiving the second report request, the server 112 can select a second machine-learning model. This second machine-learning model can be different than the first machine-learning model due to the different attribute and/or different class of the second recipient-user. The server 112 can then ingest inputs into the second machine-learning model, can received outputted text from the second machine-learning model, and can automatically generate and deliver a second message to the second recipient-user device 141 and the second recipient-user, which message can comprise all or portions of the output of the second machine-learning model. In some embodiments, the inputs ingested into the second machine-learning model relating to the subject-user can be the same inputs ingested into the first machine-learning model. However, in some embodiments, due to the selection of the second machine learning model, which second machine-learning model is different than the first machine-learning model, the outputs of the second machine-learning model can be different than the outputs of the first machine-learning model. In some embodiments, this text output of the second machine-learning model can be customized to the second recipient-user.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine-readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine-readable mediums for storing information. The term "machine-readable medium" includes, but is not limited to portable or fixed storage devices, optical storage devices, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:
1. A method for automated characterization-vector based prediction, the method comprising:

generating at a first time a characterization vector from n-dimension attributes of a first patient identified in a patient profile, the characterization vector characterizing a first patient state;

identifying a data insufficiency based on missing data in an electronic health records (EHR) database, wherein the data insufficiency prevents at least one of: complete determination of a current state of a first user; complete generation of a risk profile; or complete identification of a remediation;

provisioning a medical service corresponding to the missing data, the medical service selected to resolve the data insufficiency;

receiving from the provisioned medical service inputs indicating updates to at least one of the n-dimension attributes of the first patient;

determining a resolution of the data insufficiency based on the received inputs;

regenerating at a second time the characterization vector from the n-dimension attributes of the first patient with a first Artificial Intelligence ("AI") machine-learning model, the regenerated characterization vector charcterizing a second patient state;

generating a discrepancy vector characterizing a difference between the regenerated characterization vector and the characterization vector;

determining an efficacy of the provisioned medical service based on the discrepancy vector; and automatically identifying a second medical service for provisioning for a second patient based on the efficacy of the provisioned medical service to the first patient.

2. The method of claim 1, wherein the medical service comprises a digital component and a non-digital component for provisioning to the first patient.

3. The method of claim 2, further comprising automatically delivering the digital component of the medical service for provisioning.

4. The method of claim 3, further comprising:
receiving a patient input from a patient device implemented with a processor and a medical provider input from a provider device implemented with a processor;
identifying a first portion of the patient input as a first variable and a second portion of the patient input as a second variable; and
generating and storing the patient profile in a user profile database, wherein the patient profile identifies n-dimension attributes of a first patient.

5. The method of claim 4, wherein the digital component of the medical service for provisioning is automatically delivered subsequent to automated determination of fulfillment of at least one delivery criteria.

6. The method of claim 5, wherein the determination of fulfillment of the at least one delivery criteria is made based on data contained in a data stream received from a messaging bus, wherein the data contained in the data stream corresponds to the second variable.

7. The method of claim 6, further comprising:
upon determining resolution of the data insufficiency, identifying a second medical service comprising a second remediation to mitigate a likelihood of an adverse outcome; and
providing the second medical service to the first patient via the patient device.

8. The method of claim 7, further comprising:
identifying a first remediation to mitigate the likelihood of an adverse medical outcome identified based on the first patient state of the first patient in the patient profile, wherein the remediation is identified from a multi-dimensional network comprising a plurality of nodes linked by a plurality of edges, at least some of the nodes corresponding to a user state, a user characteristic, and a remediation, and
wherein the data insufficiency prevents identification of the first remediation.

9. The method of claim 1, wherein the first patient state comprises at least one of: a physical state; and a mental state.

10. An automated multi-dimensional network management system comprising:
a memory comprising: an electronic health records (EHR) database comprising a plurality of patient profiles; and a network database comprising a plurality of nodes linked by a plurality of edges, at least some of the nodes corresponding to a user state, and a user characteristic; and
at least one processor configured to:
generate at a first time a characterization vector from n-dimension attributes of a first patient identified in a patient profile, the characterization vector characterizing a first patient state;
identify a data insufficiency based on missing data in an electronic health records (EHR) database, wherein the data insufficiency prevents at least one of: complete determination of a current state of a first user; complete generation of a risk profile; or complete identification of a remediation;
provision a medical service corresponding to the missing data, the medical service selected to resolve the data insufficiency;
receive from the provisioned medical service inputs indicating updates to at least one of the n-dimension attributes of the first patient;
determine a resolution of the data insufficiency based on the received inputs;
regenerate at a second time the characterization vector from the n-dimension attributes of the first patient with a first Artificial Intelligence ("AI") machine-learning model, the regenerated characterization vector charcterizing a second patient state;
generate a discrepancy vector characterizing a difference between the regenerated characterization vector and the characterization vector;
determine an efficacy of the provisioned medical service based on the discrepancy vector; and
automatically identify a second medical service for provisioning for a second patient based on the efficacy of the provisioned medical service to the first patient.

11. The system of claim 10, wherein the medical service comprises a digital component and a non-digital component for provisioning to the first patient.

12. The system of claim 11, wherein the at least one processor is further configured to automatically deliver the digital component of the medical service for provisioning.

13. The system of claim 12, wherein the at least one processor is further configured to:
receive a patient input from a patient device implemented and a medical provider input from a provider device;
identify a first portion of the patient input as a first variable and a second portion of the patient input as a second variable; and
generate and store the patient profile in a user profile database, wherein the patient profile identifies n-dimension attributes of a first patient.

14. The system of claim 13, wherein the digital component of the medical service for provisioning is automatically delivered subsequent to automated determination of fulfillment of at least one delivery criteria.

15. The system of claim 14, wherein the determination of fulfillment of the at least one delivery criteria is made based on data contained in a data stream received from a messaging bus, wherein the data contained in the data stream corresponds to the second variable.

16. The system of claim 15, wherein the processor is further configured to:
   upon determining resolution of the data insufficiency, identify a second medical service comprising a second remediation to mitigate a likelihood of an adverse outcome; and
   provide the second medical service to the first patient via the patient device.

17. The system of claim 16, wherein the processor is further configured to:
   identify a first remediation to mitigate a likelihood of an adverse medical outcome identified based on the first patient state of the first patient in the patient profile, wherein the remediation is identified from the network database, and
   wherein the data insufficiency prevents identification of the first remediation.

18. The system of claim 17, wherein the first patient state comprises at least one of: a physical state; and a mental state.

\* \* \* \* \*